(12) United States Patent
Sabiston

(10) Patent No.: US 9,737,417 B2
(45) Date of Patent: Aug. 22, 2017

(54) METHOD, APPARATUS, MEDIA AND SIGNALS FOR PRODUCING A REPRESENTATION OF A MOLD

(75) Inventor: Robert Malcolm Sabiston, Vancouver (CA)

(73) Assignee: Vorum Research Corporation (CA)

( * ) Notice: Subject to any disclaimer, the term of this patent is extended or adjusted under 35 U.S.C. 154(b) by 675 days.

(21) Appl. No.: 12/670,840

(22) PCT Filed: Jul. 27, 2007

(86) PCT No.: PCT/CA2007/001337
§ 371 (c)(1),
(2), (4) Date: Jan. 26, 2010

(87) PCT Pub. No.: WO2009/015455
PCT Pub. Date: Feb. 5, 2009

(65) Prior Publication Data
US 2010/0204816 A1    Aug. 12, 2010

(51) Int. Cl.
*G06F 19/00* (2011.01)
*A61F 2/50* (2006.01)
*A61F 5/01* (2006.01)

(52) U.S. Cl.
CPC .............. *A61F 2/5046* (2013.01); *A61F 5/01* (2013.01); *A61F 2002/505* (2013.01); *A61F 2002/5047* (2013.01); *G05B 2219/35044* (2013.01)

(58) Field of Classification Search
USPC .......................................... 700/98, 163, 197
See application file for complete search history.

(56) References Cited

U.S. PATENT DOCUMENTS 4,430,718 A * 2/1984 Hendren ....................... 700/163
4,436,684 A   3/1984 White
(Continued)

FOREIGN PATENT DOCUMENTS

CA    2095238    5/1992
CA    2277093    7/1998
(Continued)

OTHER PUBLICATIONS

Harvey et al., "A Review of CAD/CAM Procedures for the Production of Custom Made Artificial Hip Joints" IEEE, 1989, p. 1938-1939.*
(Continued)

*Primary Examiner* — Robert Fennema
*Assistant Examiner* — Thomas Stevens
(74) *Attorney, Agent, or Firm* — Kolisch Hartwell, P.C.

(57) ABSTRACT

A method, apparatus, media and signals for producing a representation of a mold for forming an appliance for a living body is disclosed. The method involves identifying points representing a line corresponding to an intended edge of the appliance on a surface of the mold, the surface being defined by an input plurality of points representing a general shape of the mold. The method also involves identifying regions extending along the surface on opposite sides of the line, adjusting at least one coordinate of at least one of the input plurality of points that falls within at least one of the regions to alter the shape of the surface in the at least one region to produce a modified surface representation, and storing the modified surface representation in a computer memory to produce a modified representation of the mold.

36 Claims, 13 Drawing Sheets

(56) References Cited

U.S. PATENT DOCUMENTS

| | | | |
|---|---|---|---|
| 4,575,805 A * | 3/1986 | Moermann et al. | 700/163 |
| 4,629,409 A * | 12/1986 | Satoh et al. | 425/139 |
| 4,663,720 A * | 5/1987 | Duret et al. | 700/163 |
| 4,901,250 A * | 2/1990 | Ishida | 715/848 |
| 4,912,644 A * | 3/1990 | Aoyama et al. | 700/98 |
| 5,027,281 A * | 6/1991 | Rekow et al. | 700/182 |
| 5,056,204 A * | 10/1991 | Bartschi | 29/896.21 |
| 5,224,049 A * | 6/1993 | Mushabac | 700/163 |
| 5,237,647 A * | 8/1993 | Roberts et al. | 345/419 |
| 5,309,366 A * | 5/1994 | Grenkowitz | 700/182 |
| 5,360,446 A | 11/1994 | Kennedy | |
| 5,432,703 A * | 7/1995 | Clynch et al. | 700/163 |
| 5,452,219 A * | 9/1995 | Dehoff et al. | 700/163 |
| 5,475,613 A * | 12/1995 | Itoga et al. | 702/39 |
| 5,506,785 A * | 4/1996 | Blank et al. | 700/98 |
| 5,510,066 A | 4/1996 | Fink et al. | |
| 5,539,649 A * | 7/1996 | Walsh et al. | 700/163 |
| 5,543,103 A * | 8/1996 | Hogan et al. | 264/219 |
| 5,637,175 A * | 6/1997 | Feygin et al. | 156/264 |
| 5,742,511 A * | 4/1998 | Chasse et al. | 700/98 |
| 5,778,177 A | 7/1998 | Azar | |
| 5,824,111 A * | 10/1998 | Schall et al. | 623/33 |
| 5,876,550 A * | 3/1999 | Feygin et al. | 156/264 |
| 6,108,006 A | 8/2000 | Hoppe | |
| 6,212,441 B1 * | 4/2001 | Hazama et al. | 700/98 |
| 6,389,375 B1 | 5/2002 | Thomsen et al. | |
| 6,463,351 B1 | 10/2002 | Clynch | |
| 6,473,667 B1 | 10/2002 | Lee | |
| 6,701,200 B1 * | 3/2004 | Lukis et al. | 700/98 |
| 6,714,900 B1 * | 3/2004 | Busse et al. | 703/6 |
| 6,772,026 B2 | 8/2004 | Bradbury et al. | |
| 6,832,877 B2 * | 12/2004 | Hamada | 409/96 |
| 6,839,607 B2 * | 1/2005 | Wooten | 700/163 |
| 6,920,414 B2 * | 7/2005 | Topholm | 703/1 |
| 6,982,710 B2 | 1/2006 | Salomie | |
| 7,079,114 B1 * | 7/2006 | Smith et al. | 345/158 |
| 7,134,874 B2 * | 11/2006 | Chishti et al. | 433/24 |
| 7,167,189 B2 | 1/2007 | Di Lelle et al. | |
| 7,221,380 B2 | 5/2007 | Hunter et al. | |
| 7,299,101 B2 * | 11/2007 | Lukis et al. | 700/98 |
| 7,435,083 B2 * | 10/2008 | Chishti et al. | 433/24 |
| 8,116,900 B2 * | 2/2012 | Slemker et al. | 700/163 |
| 2001/0000805 A1 * | 5/2001 | Kadono | 700/182 |
| 2001/0002232 A1 * | 5/2001 | Young et al. | 409/132 |
| 2001/0002310 A1 * | 5/2001 | Chishti et al. | 433/24 |
| 2001/0025203 A1 * | 9/2001 | Gervasi | 700/98 |
| 2002/0013636 A1 * | 1/2002 | O'Brien et al. | 700/118 |
| 2002/0149137 A1 | 10/2002 | Jang et al. | |
| 2003/0195623 A1 | 10/2003 | Marchitto et al. | |
| 2003/0204279 A1 * | 10/2003 | Yokohari et al. | 700/98 |
| 2003/0206820 A1 | 11/2003 | Keicher et al. | |
| 2004/0068337 A1 | 4/2004 | Watson et al. | |
| 2004/0085311 A1 | 5/2004 | Lee et al. | |
| 2005/0043837 A1 * | 2/2005 | Rubbert et al. | 700/98 |
| 2005/0089213 A1 | 4/2005 | Geng | |
| 2005/0089822 A1 * | 4/2005 | Geng | 433/215 |
| 2005/0096964 A1 * | 5/2005 | Tsai | 705/10 |
| 2005/0119777 A1 | 6/2005 | Arbogast et al. | |
| 2005/0286798 A1 | 12/2005 | Pollard et al. | |
| 2006/0070260 A1 * | 4/2006 | Cavanagh et al. | 36/44 |
| 2006/0094951 A1 | 5/2006 | Dean et al. | |
| 2006/0100832 A1 | 5/2006 | Bowman | |
| 2006/0203010 A1 | 9/2006 | Kirchner et al. | |
| 2006/0286501 A1 * | 12/2006 | Chishti et al. | 433/24 |
| 2007/0118243 A1 * | 5/2007 | Schroeder et al. | 700/163 |
| 2009/0248184 A1 * | 10/2009 | Steingart et al. | 700/98 |
| 2009/0306801 A1 * | 12/2009 | Sivak et al. | 700/98 |
| 2010/0204816 A1 * | 8/2010 | Sabiston | 700/98 |

FOREIGN PATENT DOCUMENTS

| | | |
|---|---|---|
| CA | 2405738 | 10/2001 |
| EP | 1273876 A2 | 1/2003 |
| FR | 2855959 | 12/2004 |
| FR | 2885518 | 11/2006 |
| GB | 2266214 A | 10/1993 |
| JP | 03299679 A | 10/2003 |
| WO | WO8911257 | 11/1989 |
| WO | 92/08175 A1 | 5/1992 |
| WO | 94/18638 A1 | 8/1994 |
| WO | WO9718533 A1 | 5/1997 |
| WO | 02/34157 A2 | 5/2002 |
| WO | WO2004100045 A1 | 11/2004 |
| WO | WO2006110895 | 10/2006 |
| WO | WO2009015455 | 2/2009 |

OTHER PUBLICATIONS

International Searching Authority (Lucille Leonard, authorized officer); "International Search Report and the Written Opinion of the International Search Authority" for PCT/CA2007/001337; Apr. 17, 2008; 10 pages. This U.S. application is a national phase of PCT/CA2007/001337, 6 pages.

Oberg, K. et al., "The CAPOD System—A Scandinavian CAD CAM System for Prosthetic Sockets", Journal of Prosthetics and Orthotics, 1989, vol. 1, No. 3, pp. 139-148.

He et al., "A PC-based ultrasound scanning system for imaging a residual limb", Proceedings of the 16th Annual International Conference of the IEEE Engineering in Medicine and Biology Society, 1994, Baltimore, MD Nov. 3-6, 1994, pp. 480-481, vol. 1, ISBN: 0-7803-2050-6.

Jensen Nielsen, K, "Bio-Surfaces and Geometric References for a Standardized Biomechanical Design Methodology for Mass Customization", Ph.D. thesis, Brigham Young University, Apr. 2008, pp. 11-136, 185 pages.

International Search Report dated Jun. 18, 2008 in connection with related PCT Application No. PCT/CA2007/001884, 6 pages.

Anonymous, "CANFIT-PLUSTM P&O Design", posted on the internet on Oct. 15, 2006 and accessed Jun. 19, 2008 at http://web.archive.org/web/20061015183514/www.vorum.com/P&O_System/prod_P&OSystem_P&O_Design.asp?pageID=28, 2 pages.

International Search Report dated Apr. 9, 2009 in connection with related PCT Application No. PCT/CA2008/001362, 11 pages.

International Search Report dated Dec. 9, 2009 in connection with related PCT Application No. PCT/CA2009/000417, 9 pages.

A.L. Darling and W. Sun, "Orthotic design through 3D reconstruction: A passive-assistance ankle-foot orthotic", Applied Bionics and Biomechanics, Cambridge, Woodhead Publishing Ltd., vol. 3, No. 2, Jan. 1, 2006, pp. 93-99.

European Patent Office, Supplementary European Search Report and Written Opinion dated Mar. 26, 2012 in connection with related Application No. EP-21047017, 6 pgs.

Michael W. Vannier et al., "Visualization of Prosthesis Fit in Lower-Limb Amputees", IEEE Computer Graphics and Applications, Sep./Oct. 1997, pp. 16-29.

European Patent Office, "Extended European Search Report" in connection with a generally related European Patent App. No. 08783275.4, dated Nov. 6, 2013, 6 pages.

European Patent Office, "Extended Search Report" in connection with related European Patent App. No. 07785003.0, dated Oct. 23, 2013, 5 pages.

M.E. Riechmann et al., "Computer-Aided Design and Computer-Aided Manufacturing of Below-Knee Prosthetics", Proceedings of the 1991 IEEE Seventeenth Annual Northeast Bioengineering Conference, Apr. 4-5, 1991, 4 pages.

European Patent Office, "Extended European Search Report" in connection with related European Patent Application No. 09842459.1, dated Jul. 8, 2014, 7 pages.

* cited by examiner

METHOD, APPARATUS, MEDIA AND SIGNALS FOR PRODUCING A REPRESENTATION OF A MOLD

BACKGROUND OF THE INVENTION

1. Field of Invention

This invention relates generally to three-dimensional object representations and more particularly to producing a representation of a mold for forming an appliance for a living body.

2. Description of Related Art

Prostheses and orthoses are commonly produced from three-dimensional representations of a body part of a human or an animal. The three-dimensional representation may then be used to produce instructions for controlling a carving machine that is configured to carve a three-dimensional reproduction of the body part from wood or a synthetic material such as a polyurethane block.

The three-dimensional reproduction of the body part may then be used to produce an appliance to meet a patient's specific needs. For example, the three-dimensional reproduction may be used directly to produce a prosthesis, or indirectly as a mold for forming a molded orthosis. An orthosis is an appliance that is applied externally to a body part to correct deformity, improve function, or relieve symptoms of a disease by supporting or assisting the musculo-neuro-skeletal system. A prosthesis is an appliance that replaces a missing body part.

The three-dimensional representation of the body part may be produced using a non-contact optical scanner that images the body part with a high level of accuracy. The scanner may include a laser for illuminating the body part with structured light and a video camera for capturing images of the illuminated body part. The captured images may then be processed to extract three-dimensional coordinates of the surface of the body part, which may be used in turn to produce the appliance.

When producing such appliances, and in particular when producing orthoses, it may be desired to flare some of the edges of the appliance to reduce chafing and/or abrasion at the edge. Flared edges have been produced by attaching protrusions onto the three-dimensional reproduction in the vicinity of a desired edge to flare the edge of the molded appliance. Placing and attaching the protrusions is a manual task which is subject to operator error and may result in incorrectly positioned or incorrectly shaped flares in the appliance.

There remains a need for better methods and apparatus for producing appliances for a living body part.

SUMMARY OF THE INVENTION

In accordance with one aspect of the invention there is provided a method for producing a representation of a mold for forming an appliance for a living body. The method involves identifying points representing a line corresponding to an intended edge of the appliance on a surface of the mold, the surface being defined by an input plurality of points representing a general shape of the mold. The method also involves identifying regions extending along the surface on opposite sides of the line, adjusting at least one coordinate of at least one of the input plurality of points that falls within at least one of the regions to alter the shape of the surface in the at least one region to produce a modified surface representation, and storing the modified surface representation in a computer memory to produce a modified representation of the mold.

The method may involve displaying a graphical representation of the modified surface in the at least one region, the graphical representation representing a profile of the modified surface taken in a plane generally normal to the surface and extending along the surface on opposite sides of the line corresponding to the intended edge.

Displaying the graphical representation may involve displaying first and second profile portions, the first profile portion representing a profile of the modified surface up to a point coterminous with the intended edge of the appliance, and the second profile portion representing a profile of the modified surface adjacent the intended edge of the appliance.

The method may involve affecting a shape of the first profile portion in response to first user input.

The method may involve affecting a shape of the second profile portion in response to changes in the shape of the first profile portion.

Affecting the shape of the first profile portion may involve affecting the shape of the first profile portion in response to receiving user input of at least one parameter associated with the shape of the first profile portion.

Receiving user input of the at least one parameter may involve receiving at least one of a height of the intended edge of the appliance, a setback distance from the intended edge of the appliance, an angle of the first profile portion at the intended edge of the appliance, a tension parameter that affects the straightness of the first profile portion proximate the intended edge, and a tension parameter that affects the straightness of the first profile portion distal to the intended edge.

The first profile portion may be represented by a curve defined by a plurality of control points located on or proximate the curve and affecting the shape of the first profile portion may involve affecting the shape of the first profile portion in response to user input representing desired changes in locations of respective control points.

The method may involve affecting a shape of the second profile portion in response to second user input.

The method may involve receiving the input plurality of points representing the general shape of the mold.

The method may involve interpolating between points in the input plurality of points to produce an intermediate plurality of points representing the general shape of the mold, the intermediate plurality of points having a greater number of points than the input plurality of points.

Storing the modified surface to produce the modified representation of the mold may involve storing an output plurality of points representing the modified representation of the mold, the output plurality of points having a number of points less than the intermediate plurality of points.

Receiving the input plurality of points may involve receiving a plurality of points from a three-dimensional surface scanner, the plurality of points representing at least one surface of the living body for which the appliance may be intended.

The method may involve transforming the modified representation of the mold into a set of instructions operable to control a computer aided manufacturing machine to produce the mold.

The method may involve forming the appliance on the mold, and transforming the points representing the line corresponding to an intended edge of the appliance on a surface of the mold into a set of instructions operable to control a computer aided manufacturing machine for trimming the appliance along the intended edge while mounted on the mold.

Identifying the points representing the line may involve displaying a representation of the surface, and identifying a plurality of points on the displayed representation of the surface, the plurality of points representing the line.

Identifying the plurality of points may involve selecting points in response to user input indicating desired locations of the points on the displayed representation of the surface.

The method may involve segmenting the line into a plurality of straight line segments, each straight line segment being defined between adjacent points on the line.

The method may involve interpolating between the points on the line before segmenting the line.

Identifying the regions may involve identifying a plurality of polygonal regions along the line.

Identifying the polygonal regions may involve identifying at least one quadrilateral shaped region along the line.

Identifying the at least one quadrilateral shaped region may involve identifying a first vertex and a second vertex of the quadrilateral shaped region, the first and second vertices being coincident with adjacent ones of the points representing the line, identifying a third vertex of the quadrilateral shaped region, the third vertex being spaced apart from the first vertex in a direction normal to the line at the first vertex, and identifying a fourth vertex of the quadrilateral shaped region, the fourth vertex being spaced apart from the second vertex in a direction normal to the line at the second vertex.

Identifying the third and fourth vertices may involve identifying third and fourth vertices spaced apart from the respective first and second vertices by a setback distance.

The method may involve receiving user input of the setback distance.

The method may involve identifying at least one point on the surface that falls within the polygonal region.

The method may involve receiving at least one parameter defining a desired alteration to the shape of the surface and adjusting may involve using the at least one parameter to compute the at least one coordinate.

Adjusting may involve adjusting the at least one coordinate to cause the modified surface to be extended outwardly from the surface.

Adjusting may involve adjusting at least one coordinate of ones of the input plurality of points that fall within respective ones of the plurality of regions to produce a modified surface representation in memory, the modified surface representation having an outwardly extending contour along the line.

In accordance with another aspect of the invention there is provided a computer readable medium encoded with codes for directing a processor circuit to produce a representation of a mold for forming an appliance for a living body. The codes direct the processor circuit to identify points representing a line corresponding to an intended edge of the appliance on a surface of the mold, the surface being defined by an input plurality of points representing a general shape of the mold. The codes also direct the processor circuit to identify regions extending along the surface on opposite sides of the line, to adjust at least one coordinate of at least one of the input plurality of points that falls within at least one of the regions to alter the shape of the surface in the at least one region to produce a modified surface representation in memory, and to store the modified surface representation in a computer memory to produce a modified representation of the mold.

In accordance with another aspect of the invention there is provided a computer readable signal encoded with codes for directing a processor circuit to produce a representation of a mold for forming an appliance for a living body. The codes direct the processor circuit to identify points representing a line corresponding to an intended edge of the appliance on a surface of the mold, the surface being defined by an input plurality of points representing a general shape of the mold. The codes also direct the processor circuit to identify regions extending along the surface on opposite sides of the line, to adjust at least one coordinate of at least one of the input plurality of points that falls within at least one of the regions to alter the shape of the surface in the at least one region to produce a modified surface representation in memory, and to store the modified surface representation in a computer memory to produce a modified representation of the mold.

In accordance with another aspect of the invention there is provided an apparatus for producing a representation of a mold for forming an appliance for a living body. The apparatus includes provisions for identifying points representing a line corresponding to an intended edge of the appliance on a surface of the mold, the surface being defined by an input plurality of points representing a general shape of the mold. The apparatus also includes provisions for identifying regions extending along the surface on opposite sides of the line, provisions for adjusting at least one coordinate of at least one of the input plurality of points that falls within at least one of the regions to alter the shape of the surface in the at least one region to produce a modified surface representation in memory, and provisions for storing the modified surface representation to produce a modified representation of the mold.

The apparatus may include provisions for displaying a graphical representation of the modified surface in the at least one region, the graphical representation representing a profile of the modified surface taken in a plane generally normal to the surface and extending along the surface on opposite sides of the line corresponding to the intended edge.

The provisions for displaying the graphical representation may include provisions for displaying first and second profile portions, the first profile portion representing a profile of the modified surface up to a point coterminous with the intended edge of the appliance, and the second profile portion representing a profile of the modified surface adjacent the intended edge of the appliance.

The apparatus may include provisions for affecting a shape of the first profile portion in response to first user input.

The apparatus may include provisions for affecting a shape of the second profile portion in response to changes in the shape of the first profile portion.

The provisions for affecting the shape of the first profile portion may include provisions for affecting the shape of the first profile portion in response to receiving user input of at least one parameter associated with the shape of the first profile portion.

The provisions for receiving user input of the at least one parameter may include provisions for receiving at least one of a height of the intended edge of the appliance in the at least one region, a setback distance from the intended edge of the appliance, an angle of the first profile portion at the intended edge of the appliance, a tension parameter that affects the straightness of the first profile portion proximate the intended edge, and a tension parameter that affects the straightness of the first profile portion distal to the intended edge.

The first profile portion may be represented by a curve defined by a plurality of control points located on or proximate the curve and the provisions for affecting the shape of the first profile portion may include provisions for affecting the shape of the first profile portion in response to user input representing desired changes in locations of respective control points.

The apparatus may include provisions for affecting a shape of the second profile portion in response to second user input.

The apparatus may include provisions for receiving the input plurality of points representing the general shape of the mold.

The apparatus may include provisions for interpolating between points in the input plurality of points to produce an intermediate plurality of points representing the general shape of the mold, the intermediate plurality of points having a greater number of points than the input plurality of points.

The provisions for storing the modified surface to produce the modified representation of the mold may include provisions for storing an output plurality of points representing the modified representation of the mold, the output plurality of points having a number of points less than the intermediate plurality of points.

The provisions for receiving the input plurality of points may include provisions for receiving a plurality of points from a three-dimensional surface scanner, the plurality of points representing at least one surface of the living body for which the appliance may be intended.

The apparatus may include provisions for transforming the modified representation of the mold into a set of instructions operable to control a computer aided manufacturing machine to produce the mold.

The apparatus may include provisions for forming the appliance on the mold, and provisions for transforming the points representing the line corresponding to an intended edge of the appliance on a surface of the mold into a set of instructions operable to control a computer aided manufacturing machine for trimming the appliance along the intended edge while mounted on the mold.

The provisions for identifying the points representing the line may include provisions for displaying a representation of the surface, and provisions for identifying a plurality of points on the displayed representation of the surface, the plurality of points representing the line.

The provisions for identifying the plurality of points may include provisions for selecting points in response to user input indicating desired locations of the points on the displayed representation of the surface.

The apparatus may include provisions for segmenting the line into a plurality of straight line segments, each straight line segment being defined between adjacent points on the line.

The apparatus may include provisions for interpolating between the points on the line before segmenting the line.

The provisions for identifying the regions may include provisions for identifying a plurality of polygonal regions along the line.

The provisions for identifying the polygonal regions may include provisions for identifying at least one quadrilateral shaped region along the line.

The provisions for identifying the at least one quadrilateral shaped region may include provisions for identifying a first vertex and a second vertex of the quadrilateral shaped region, the first and second vertices being coincident with adjacent ones of the points representing the line, provisions for identifying a third vertex of the quadrilateral shaped region, the third vertex being spaced apart from the first vertex in a direction normal to the line at the first vertex, and provisions for identifying a fourth vertex of the quadrilateral shaped region, the fourth vertex being spaced apart from the second vertex in a direction normal to the line at the second vertex.

The provisions for identifying the third and fourth vertices may include provisions for identifying third and fourth vertices spaced apart from the respective first and second vertices by a setback distance.

The apparatus may include provisions for receiving user input of the setback distance.

The apparatus may include provisions for identifying at least one point on the surface that falls within the polygonal region.

The apparatus may include provisions for receiving at least one parameter defining a desired alteration to the shape of the surface and the provisions for adjusting may include provisions for using the at least one parameter to compute the at least one coordinate.

The provisions for adjusting may include provisions for adjusting the at least one coordinate to cause the modified surface to be extended outwardly from the surface.

The provisions for adjusting may include provisions for adjusting at least one coordinate of ones of the input plurality of points that fall within respective ones of the plurality of regions to produce a modified surface representation in memory, the modified surface representation having an outwardly extending contour along the line.

In accordance with another aspect of the invention there is provided an apparatus for producing a representation of a mold for forming an appliance for a living body. The apparatus includes a processor circuit operably configured to identify points representing a line corresponding to an intended edge of the appliance on a surface of the mold, the surface being defined by an input plurality of points representing a general shape of the mold. The apparatus also includes identify regions extending along the surface on opposite sides of the line, adjust at least one coordinate of at least one of the input plurality of points that falls within at least one of the regions to alter the shape of the surface in the at least one region to produce a modified surface representation in memory, and store the modified surface representation in a computer memory to produce a modified representation of the mold.

The processor circuit may be operably configured to display a graphical representation of the modified surface in the at least one region, the graphical representation representing a profile of the modified surface taken in a plane generally normal to the surface and extending along the surface on opposite sides of the line corresponding to the intended edge.

The processor circuit may be operably configured to display first and second profile portions, the first profile portion representing a profile of the modified surface up to a point coterminous with the intended edge of the appliance, and the second profile portion representing a profile of the modified surface adjacent the intended edge of the appliance.

The processor circuit may be operably configured to affect a shape of the first profile portion in response to first user input.

The processor circuit may be operably configured to affect a shape of the second profile portion in response to changes in the shape of the first profile portion.

The processor circuit may be operably configured to affect the shape of the first profile portion in response to receiving user input of at least one parameter associated with the shape of the first profile portion.

The processor circuit may be operably configured to receive at least one of a height of the intended edge of the appliance in the at least one region, a setback distance from the intended edge of the appliance, an angle of the first profile portion at the intended edge of the appliance, and a tension parameter that affects the straightness of the first profile portion proximate the intended edge, and a tension parameter that affects the straightness of the first profile portion distal to the intended edge.

The first profile portion may be represented by a curve defined by a plurality of control points located on or proximate the curve and the processor circuit may be operably configured to affect the shape of the first profile portion in response to user input representing desired changes in locations of respective control points.

The processor circuit may be operably configured to affect a shape of the second profile portion in response to second user input.

The processor circuit may be operably configured to receive the input plurality of points representing the general shape of the mold.

The processor circuit may be operably configured to interpolate between points in the input plurality of points to produce an intermediate plurality of points representing the general shape of the mold, the intermediate plurality of points having a greater number of points than the input plurality of points.

The processor circuit may be operably configured to store an output plurality of points representing the modified representation of the mold, the output plurality of points having a number of points less than the intermediate plurality of points.

The processor circuit may be operably configured to receive a plurality of points from a three-dimensional surface scanner, the plurality of points representing at least one surface of the living body for which the appliance may be intended.

The processor circuit may be operably configured to transform the modified representation of the mold into a set of instructions operable to control a computer aided manufacturing machine to produce the mold.

The processor circuit may be operably configured to transform the points representing the line corresponding to an intended edge of the appliance on a surface of the mold into a set of instructions operable to control a computer aided manufacturing machine for trimming a formed appliance along the intended edge while mounted on the mold.

The processor circuit may be operably configured to identify the points representing the line by displaying a representation of the surface, and identifying a plurality of points on the displayed representation of the surface, the plurality of points representing the line.

The processor circuit may be operably configured to identify the plurality of points by selecting the points in response to user input indicating desired locations of the points on the displayed representation of the surface.

The processor circuit may be operably configured to segment the line into a plurality of straight line segments, each straight line segment being defined between adjacent points on the line.

The processor circuit may be operably configured to interpolate between the points on the line before segmenting the line.

The processor circuit may be operably configured to identify a plurality of polygonal regions along the line.

The processor circuit may be operably configured to identify at least one quadrilateral shaped region along the line.

The processor circuit may be operably configured to identify the at least one quadrilateral shaped region by identifying a first vertex and a second vertex of the quadrilateral shaped region, the first and second vertices being coincident with adjacent ones of the points representing the line, identifying a third vertex of the quadrilateral shaped region, the third vertex being spaced apart from the first vertex in a direction normal to the line at the first vertex, and identifying a fourth vertex of the quadrilateral shaped region, the fourth vertex being spaced apart from the second vertex in a direction normal to the line at the second vertex.

The processor circuit may be operably configured to identify third and fourth vertices spaced apart from the respective first and second vertices by a setback distance.

The processor circuit may be operably configured to receive user input of the setback distance.

The processor circuit may be operably configured to identify at least one point on the surface that falls within the polygonal region.

The processor circuit may be operably configured to receive at least one parameter defining a desired alteration to the shape of the surface and the provisions for adjusting may include provisions for using the at least one parameter to compute the at least one coordinate.

The processor circuit may be operably configured to adjust the at least one coordinate to cause the modified surface to be extended outwardly from the surface.

The processor circuit may be operably configured to adjust at least one coordinate of ones of the input plurality of points that fall within respective ones of the plurality of regions to produce a modified surface representation in memory, the modified surface representation having an outwardly extending contour along the line.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION

Figure 1:
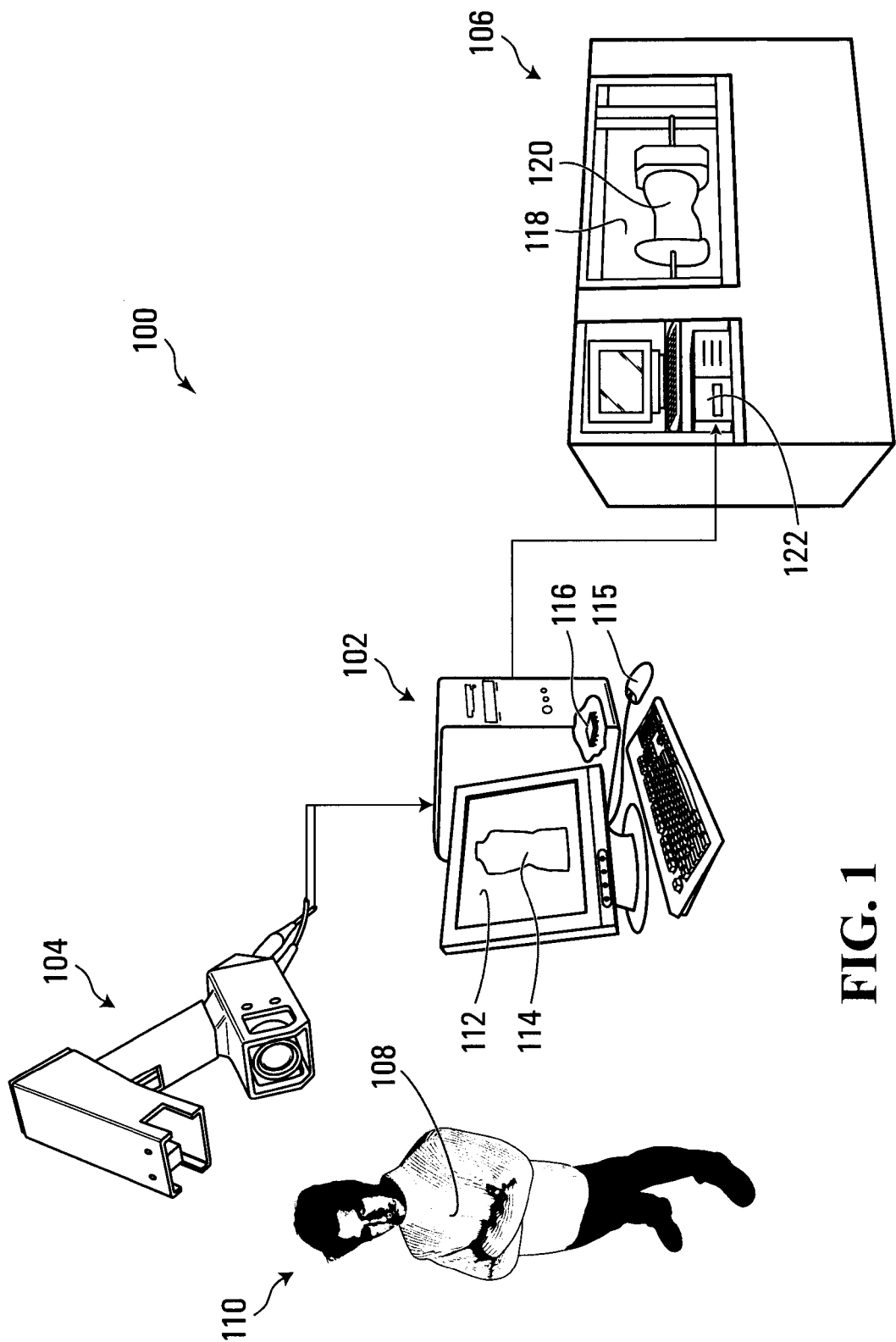
FIG. 1 is a schematic view of a system for producing an appliance for a living body.

Referring to FIG. 1, a CAD/CAM (computer aided design/computer aided manufacturing) system for producing an appliance for a living body is shown generally at 100. The system 100 includes an apparatus 102 for producing a representation of a mold, a scanner 104 and a computer aided manufacturing (CAM) machine 106.

The apparatus 102 is in communication with the scanner 104 for receiving a signal encoded with an input plurality of points representing a general surface shape of a part of a living body for which a mold is to be produced. In the embodiment shown in FIG. 1, the body part is a torso 108 of a patient 110 but in other embodiments the body part may be any part of a living body. Examples of suitable scanners include the FastSCAN Cobra handheld scanner manufactured by Polhemus of Colchester, Vt., the Yeti Foot Scanner manufactured by Vorum Research Corporation of British Columbia, Canada, and the STARscanner™ manufactured by Orthomerica Inc. of California.

The apparatus 102 further includes a display 112 for displaying a representation 114 of the torso 108, and a processor circuit 116 for manipulating the input plurality of points and/or the displayed representation of the torso. In this embodiment the apparatus 102 also includes a pointing device 115 having one or more actuator buttons for receiving user input.

In general, when producing an appliance such as a prosthesis or orthosis, the input plurality of points from the scanner 104 may be used as a starting point to which modifications are made using the apparatus 102 to produce a modified surface representation. The modified surface representation includes alterations to the shape of the surface, such as compressions in areas of the body that tolerate pressure and/or relief in certain areas of the body that are sensitive to pressure, thus providing a comfortably fitting appliance defined by the modified surface representation.

The CAM machine 106 generally includes a machine tool portion 118 for machining the mold from a material such as polyurethane foam or wood, for example. The machined mold has a shape defined by the modified surface representation and generally corresponds to the shape of the body part, with alterations for comfort and/or support.

The CAM machine 106 also includes a controller 122 for controlling the machine tool portion of the CAM machine. The controller 122 is in communication with the apparatus 102 for receiving a signal encoded with instructions operable to control the CAM machine 106 for producing a machined mold 120 (in this case the torso 108 of the patient 110). An example of a suitable CAM machine is the CANFIT-PLUS™ Carver produced by Vorum Research Corporation of British Columbia, Canada.

The machined mold 120 may then be used to form the appliance, such as an orthosis, by molding a thermoplastic or other material over the machined reproduction. Once sufficiently cured on the mold 120, the appliance may be removed and, if necessary, trimmed or otherwise processed to from the final appliance.

Processor Circuit

Figure 2:
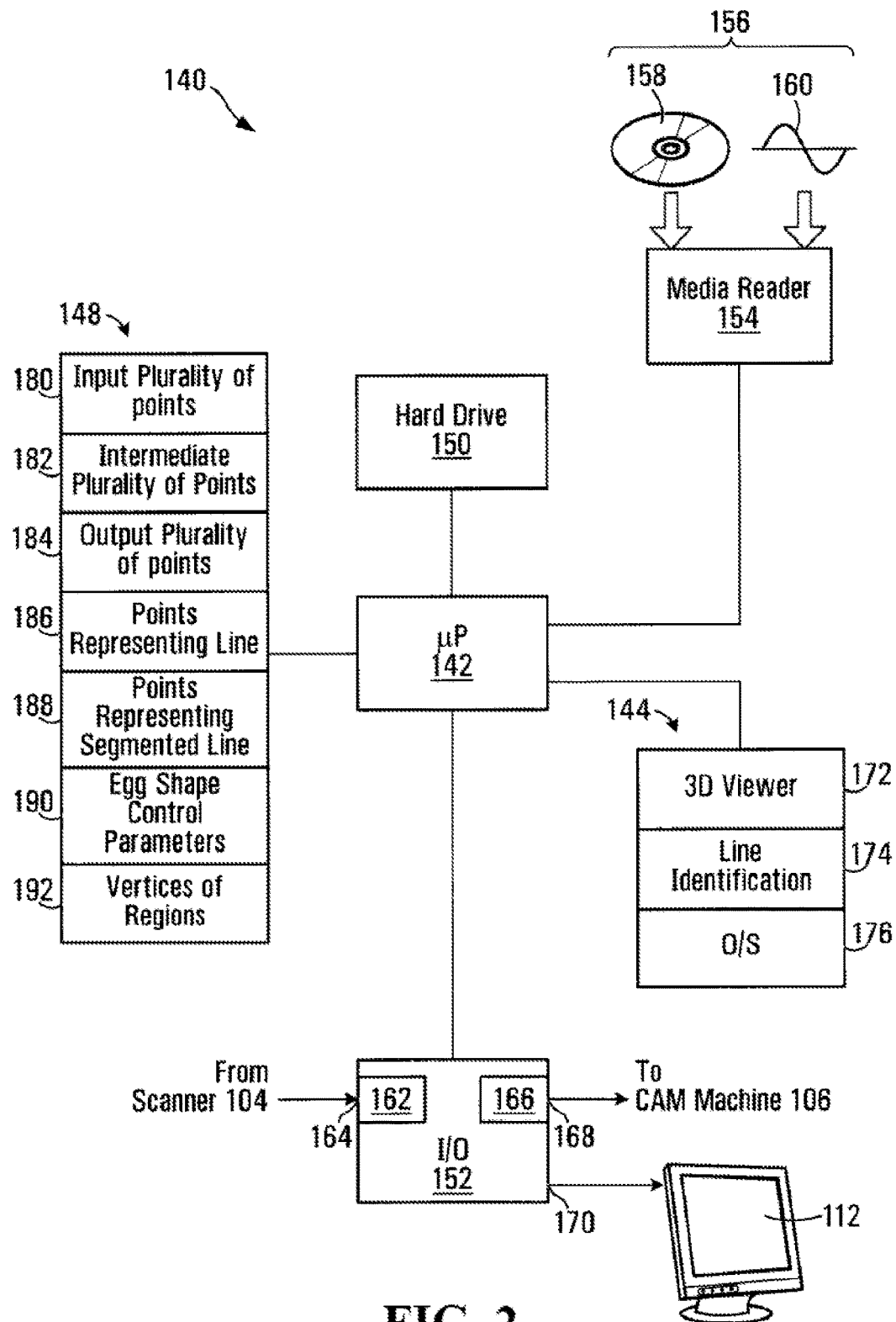
FIG. 2 is a schematic view of a processor circuit for implementing an apparatus for producing a representation of a mold in accordance with an embodiment of the invention.

Referring to FIG. 2, the processor circuit 116 of the apparatus 102 is shown in greater detail at 140. The processor circuit 140 includes a microprocessor 142, a program memory 144, a random access memory (RAM) 148, a hard drive 150, an input output port (I/O) 152, and a media reader 154, all of which are in communication with the microprocessor 142.

Program codes for directing the microprocessor 142 to carry out various functions are stored in the program memory 144, which may be implemented as a random access memory (RAM) and/or a hard disk drive (HDD), or a combination thereof. The program memory 144 includes a block of codes 172 for directing the microprocessor 142 to provide functions for producing a three-dimensional (3D) representation of the torso 108 on the display 112. The program memory 144 also includes a block of codes 174 for directing the microprocessor 142 provide functions for identifying a line corresponding to an intended edge of the appliance, and a block of codes 176 for directing the microprocessor to provide general operating system (O/S) functions.

The media reader 154 facilitates loading program codes into the program memory 144 from a computer readable medium 156, such as a CD ROM disk 158, or a computer readable signal 160, such as may be received over a network such as the internet, for example.

The RAM 148 includes a plurality of storage locations including a store 180 for storing the input plurality of points representing a shape of the body part (for example the torso 108) for which it is desired to produce a mold. The RAM 148 also includes a store 182 for storing an intermediate plurality of points including the input plurality of points and interpolated points in-between the input plurality of points. The RAM 148 also includes a store 184 for storing an output plurality of points representing a modified representation of the mold. The RAM 148 also includes a store 186 for storing points representing the line corresponding to the intended edge of the appliance, and a store 188 for storing points representing a segmented line corresponding to the intended edge of the appliance. The RAM 148 further includes a store 190 for storing edge shape control parameters, and a store 192 for storing vertices of regions, as described later herein.

The I/O 152 includes a first interface 162 having an input 164 for receiving the signal encoded with the input plurality of points representing the shape of the torso 108, and a second interface 166 having an output 168 for producing the signal encoded with the instructions for controlling the CAM machine 106. The interfaces 162 and 166 may be universal serial bus (USB) or an RS232 serial interface for example. The I/O 152 also includes an output 170 for producing a display signal for causing a representation of the torso 108 to be displayed on the display 112.

Data Representation of the Body Part

The scanner 104 shown in FIG. 1 may be configured to produce data representing the torso 108 in any of a number of existing data formats for representing surfaces of 3D objects. In one embodiment the surface of the torso 108 may be represented as a wireframe mesh of polygons, in which case a representative data file may include an ordered list x, y, and z Cartesian coordinates (x,y,z) defining vertices of the polygons making up the wireframe mesh.

Figure 3:
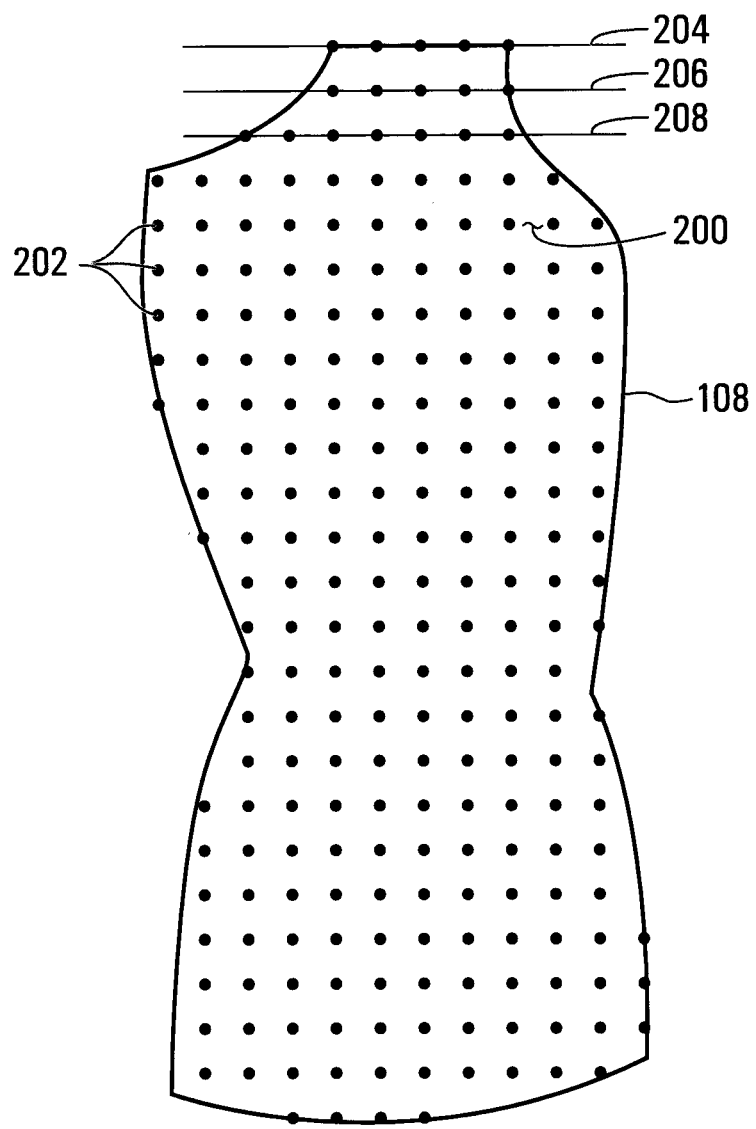
FIG. 3 is a front perspective view of an exemplary torso body part representation.

Referring to FIG. 3, in an exemplary embodiment, a surface 200 of the torso 108 is represented by a plurality of points 202 produced by the scanner 104, each point having associated (x,y,z) coordinates. In this embodiment, the data representation is ordered in a plurality of planes or slices, of which three exemplary planes 204, 206 and 208 are shown. Each plane 204-208 includes a plurality of co-planar points 202, and (x,y,z) coordinates of the points making up each plane may be stored as a row in a data array of at least two dimensions (not shown). Subsequent planes may be represented as successive rows in the data array. In the embodiment shown in FIG. 3, planes 204-208 are parallel to each other but in other embodiments the planes may be disposed at an angle to each other.

Figure 4:
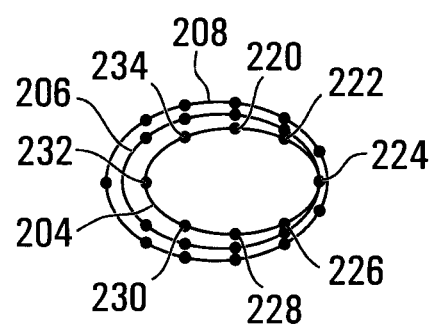
FIG. 4 is a top view of the exemplary torso body part representation shown in FIG. 3.

Referring to FIG. 4, the planes 204-208 are shown in plan view. Each plane is represented by points 202 on the surface 200 of the torso 108. For example the plane 204 includes points 220-234, which may be stored as a row in a first row of a two dimensional data array as values $A_{1,1}$, $A_{1,2}$, $A_{1,3}$, $A_{1,4}$, $A_{1,5}$, $A_{1,6}$, $A_{1,7}$, and $A_{1,5}$, where each A value is a number representing (x,y,z) coordinates of the point on the plane 204. Subsequent planes 206 and 208 are represented by subsequent rows in the data array.

Alternatively a three-dimensional data array may be used with each respective x, y and z coordinate being stored as separate value in the three-dimensional data array.

Operation

Figure 5:
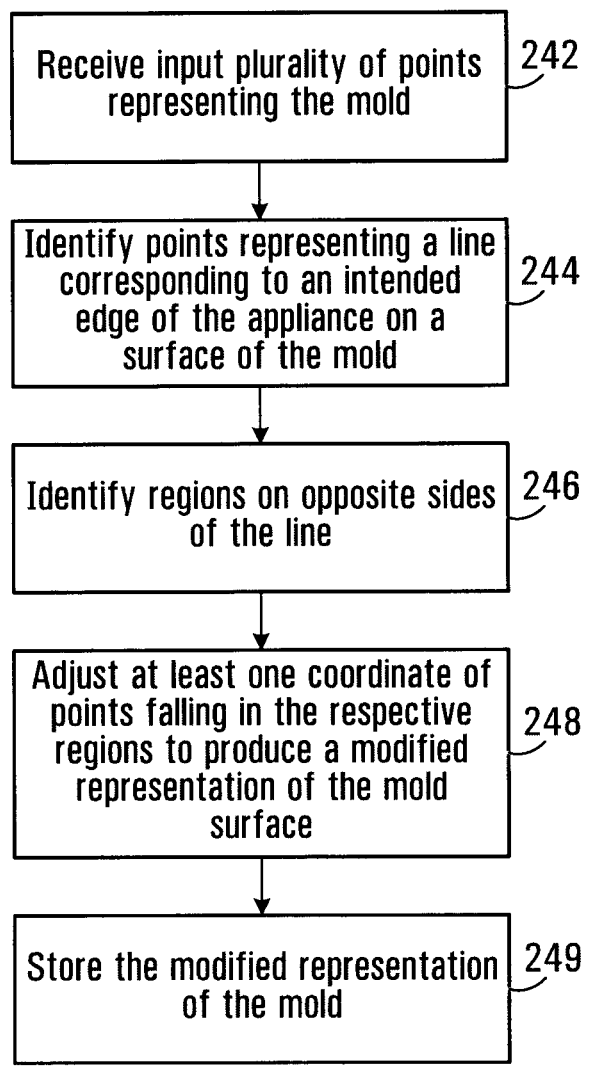
FIG. 5 is a flowchart representing blocks of codes for directing the processor circuit shown in FIG. 2 to produce a representation of a mold.

Referring to FIG. 5, a flowchart of blocks of codes for directing the microprocessor 142 (shown in FIG. 2) to produce a representation of a mold for forming an appliance for a living body, is shown generally at 240. The actual code to implement each block may be written in any suitable program language, such as C, and/or C++, for example.

The process begins at block 242, which directs the microprocessor 142 to receive the input plurality of points representing the mold. Block 244 then directs the microprocessor 142 to identify points representing a line corresponding to an intended edge of the appliance on a surface of the mold. The surface is defined by the input plurality of points representing the general shape of the mold.

Block 246 then directs the microprocessor 142 to identify regions extending along the surface on opposite sides of the line.

The process then continues at block 248, which directs the microprocessor 142 to adjust at least one coordinate of at least one of the input plurality of points that falls within at least one of the regions to alter the shape of the surface in the at least one region to produce a modified surface representation.

Block 249 then directs the microprocessor 142 to store the modified surface in memory to produce the modified representation of the mold.

Receiving the Input Plurality of Points

Figure 6:
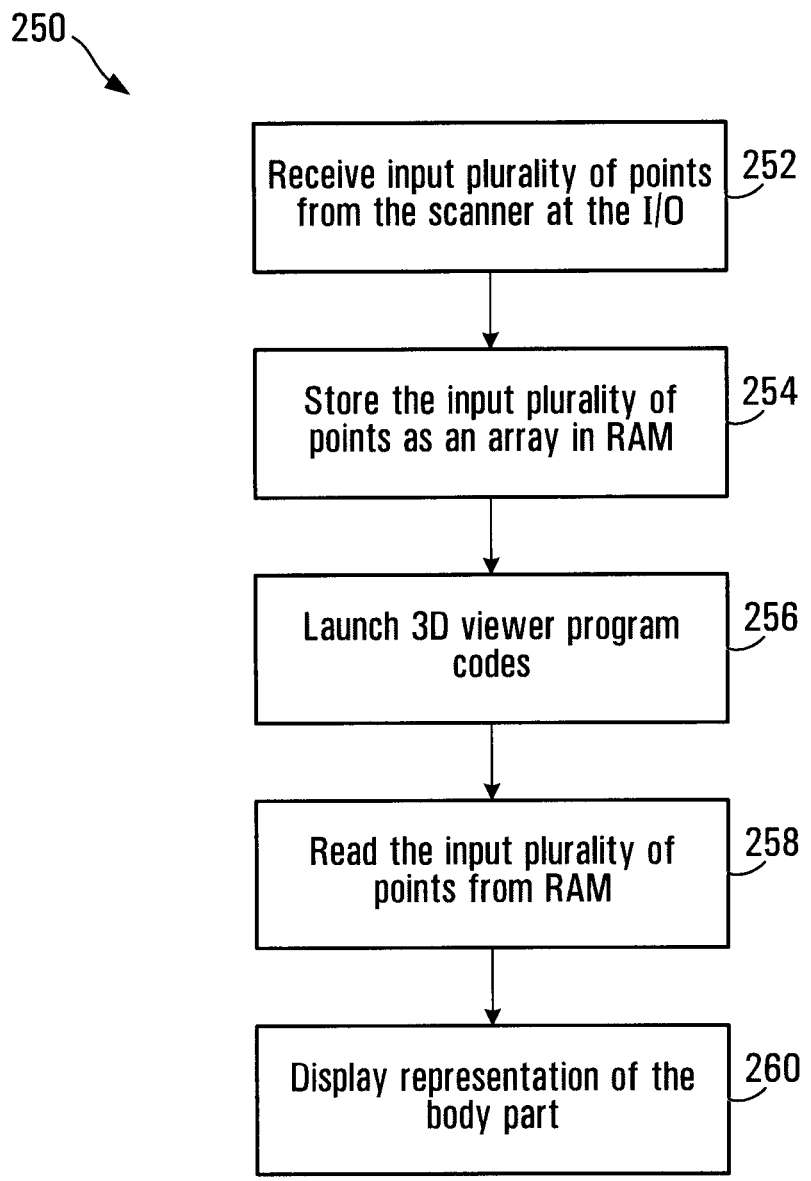
FIG. 6 is a flowchart representing blocks of codes for directing the processor circuit shown in FIG. 2 to receive the input plurality of points representing a body part.

Block 242 of the process 240 is shown in greater detail in FIG. 6. Referring to FIG. 6, a flowchart of blocks of codes for directing the microprocessor 142 (shown in FIG. 2) to receive the input plurality of points is shown generally at 250.

The process begins at block 252, which directs the microprocessor 142 to cause the I/O 152 to receive a signal encoded with data defining the input plurality of data points from the scanner 104 at the interface 162.

Block 254 then directs the microprocessor 142 to store the data points as a two dimensional array in the store 180 of the RAM 148.

Block 256 then directs the microprocessor 142 to launch the 3D viewer program codes 172 in the program memory 144. At block 258, the 3D viewer program codes 172 direct the microprocessor 142 to read the input plurality of points from the store 180 in the RAM 148.

Block 260 then directs the microprocessor 142 to display a representation of the body part on the display 112. In general the 3D viewer program codes 172 direct the microprocessor 142 to provide functions for viewing the body part, such as the torso 108, from a perspective point which may be selected in response to user input (received at the pointing device 115 for example), thus facilitating viewing of the body part from a plurality of different angles. The 3D viewer program codes 172 may also provide functions such as shading of the polygon mesh to provide a more realistic view of the object than is provided by a conventional wireframe view.

Figure 7:
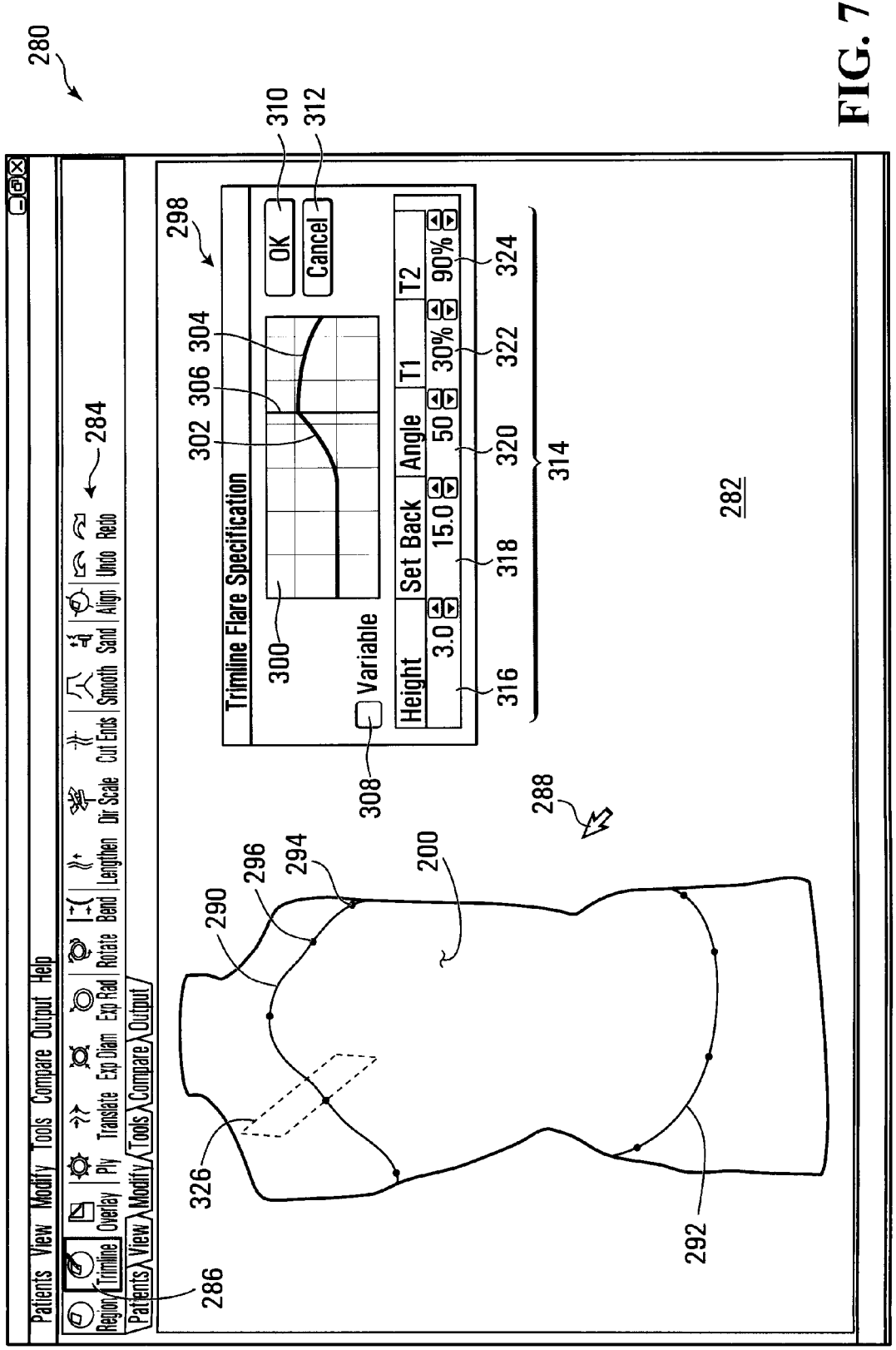
FIG. 7 is a screenshot of a view of the exemplary torso body part representation shown in FIGS. 3 and 4.

An exemplary screenshot of a representative view of the body part is shown in FIG. 7 generally at 280. The view 280 includes a display area 282 for displaying the 3D representation of the torso 108, which in this case is displayed as a shaded polygon mesh. The view 280 also includes a control panel 284. The control panel 284 includes various control buttons for manipulating the displayed view, including a "trimline" button 286 for invoking the line identification program codes 174 (shown in FIG. 2).

The microprocessor 142 further causes a cursor 288 to be displayed on the view 280. The operating system program codes 174 include codes for directing the microprocessor 142 to cause the cursor 288 to move in response to user input received at the pointing device 115.

In the view 280, a line 290 and a line 292 are also displayed to represent desired edges for the appliance that is being produced, and a popup window 298 may also be displayed on the display area 282, as described later herein.

Line Identification

Figure 8:
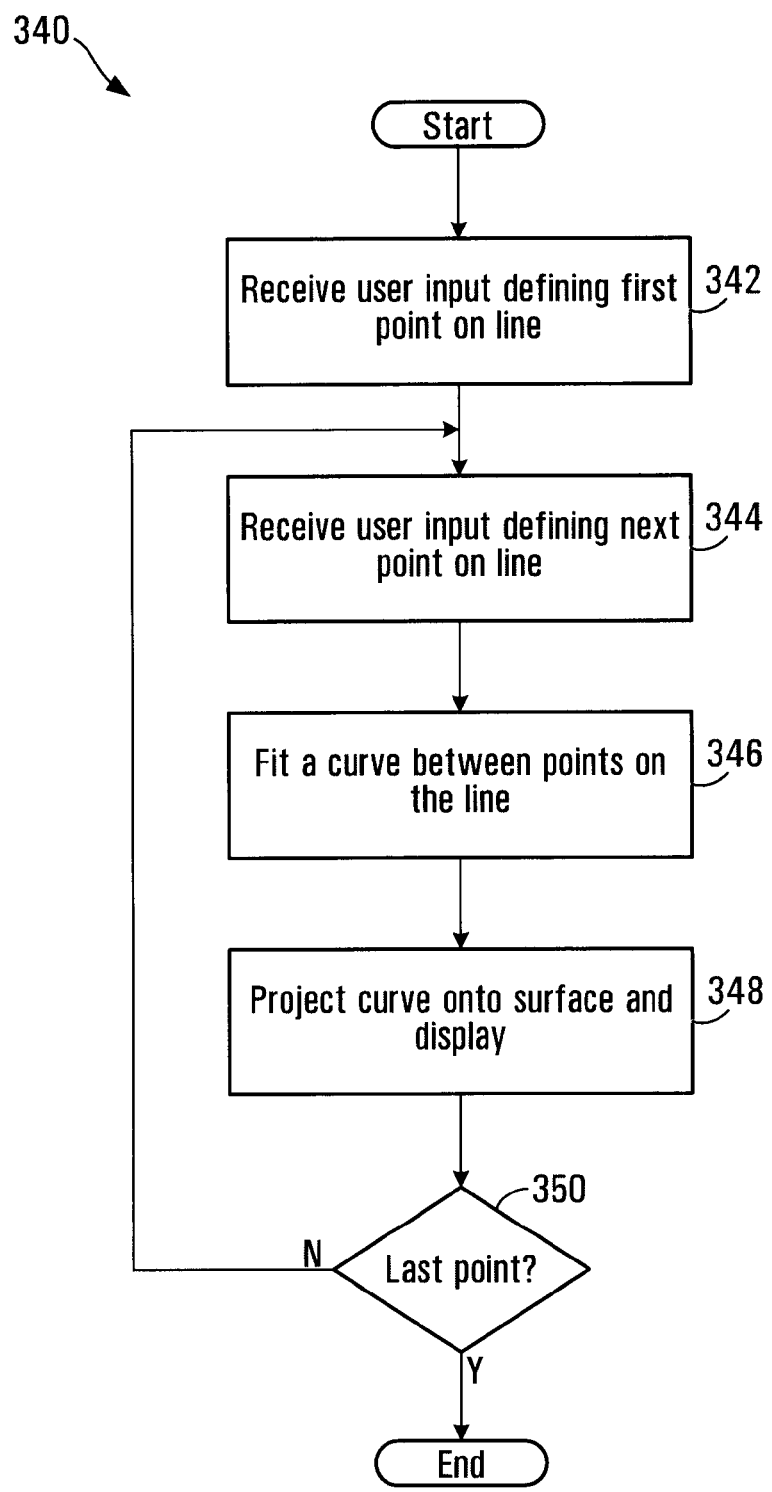
FIG. 8 is a flowchart representing blocks of codes for directing the processor circuit shown in FIG. 2 to execute a process for identifying lines representing edges of an appliance to be produced.

Referring back to FIG. 5, block 244 of the process 240 is shown in greater detail in FIG. 8. Referring to FIG. 8, a flowchart of blocks of codes for directing the microprocessor 142 (shown in FIG. 2) to execute a process for identifying the lines 290 and 292 is shown generally at 340. The process 340 starts when the "trimline" button 286 (shown in FIG. 7) is actuated by the user, which causes the line identification program codes 174 to be launched.

The process begins at block 342, which directs the microprocessor 142 to receive user input identifying a first point representing the line. In this embodiment, the user input is received from the pointing device 115 of the apparatus 102 when the user of the apparatus 102 moves the cursor 288 to a desired location for the point and actuates the actuator button on the pointing device 115. Referring to back FIG. 7, the first point on the line 290 may be a point 294, and may be identified by a dot displayed at the selected location on the display area.

The process 340 then continues at block 344, which directs the microprocessor 142 to receive user input identifying a next point representing the line (in this case a point 296 shown in FIG. 7).

Block 346 then directs the microprocessor 142 to fit a line between the points 294 and 296. Block 348 then directs the microprocessor 142 to project the curve onto the surface 200 and to display the line on the display area 282. At this time, since only two points 294 and 296 have been received, the line joining the points is a straight line, but when projected onto a non-planar surface will be appear as the curved line 290 on the surface 200.

Block 350 then directs the microprocessor 142 to determine whether the point 296 was the last point. If the point 296 was not the last point, then block 350 directs the microprocessor 142 to return to block 344 to receive further points. As points are received, the fitted line between points is adjusted to pass through each of the identified points. In one embodiment curve fitting involves fitting a plurality of piecewise splines through the identified points to produce a smooth line 290. As each point is added, the fitted curve is updated and thus the line 290 may change shape as points are added.

In most embodiments, the lines 290 and 292 may extend around the back of the torso 108, and accordingly, when points have been identified across the front surface of the torso as displayed in FIG. 7, the user may provide user input to cause the representation of the torso to be rotated to allow identification of further points around the torso. In some embodiments the line 290 may be joined to form a closed loop in response to the user actuating the actuator button on the pointing device 115 when the cursor 288 is in the vicinity of the first point 294. In other embodiments the lines 290 or 292 may be have open ends where the ends terminate at on the torso 108 at a truncation plane (such as the plane 204 shown in FIG. 3).

If at block 350 the point is the last point then the process 340 ends. The last point may be identified by the user pressing an actuator button on the pointing device 115 or by pressing a key on a keyboard, for example.

Advantageously, the identification of the lines 290 and 292 is performed interactively, and the process 340 may further permit locations of points on the lines 290 and 292 to be changed in response to user input to facilitate editing of the appearance of the lines on the torso 108.

Graphical Preview Window

The lines 290 and 292 correspond to edges along which it is desired to shape the appliance to provide a comfortable fit to the living body. Referring back to FIG. 7, the window 298 generally displays a graphical representation of the shape of the mold in the region of the edge, which facilitates previewing the edge shape before the appliance is produced.

The window 298 includes a graphical representation 300, which has a first profile portion 302, a second profile portion 304 and a separator 306. The separator 306 is a vertical line which indicates a location coterminous with the intended edge of the appliance on the body part. The graphical representation 300 generally corresponds to a cross sectional view of a surface of the mold taken in a plane generally normal to the surface of the mold and extending along the surface on opposite sides of the line, as generally indicated by the broken line 326.

The graphical representation 300 is generally associated with at least one of the points on the lines 290 and 292. The window 298 also includes a "variable" checkbox 308, which when checked allows definition of a varying edge shape along the line 290 or 292. The window 298 also includes an "OK" command button 310 and a "Cancel" command button 312 for respectively accepting or cancelling changes represented by the graphical representation 300 of the edge shape.

In the embodiment shown the window 298 further includes parametric controls 314 for affecting the shape of the first profile portion 302 and the second profile portion 304. The parametric controls 314 include a height field 316 for entering a height of the first profile portion 302 at the separator 306, a setback field 318 for entering a setback distance from the separator, an angle field 320 for entering an angle of the first profile portion to the separator, and T1 and T2 tension parameter fields 322 and 324 for entering tension parameters that generally affect the straightness of the first profile portion.

In this embodiment the parametric controls 314 all affect the shape of the first profile portion 302. In other embodiments, additional setback, angle, and tension parameter fields (not shown) may be included for affecting the shape of the second profile portion 304.

Figure 9:
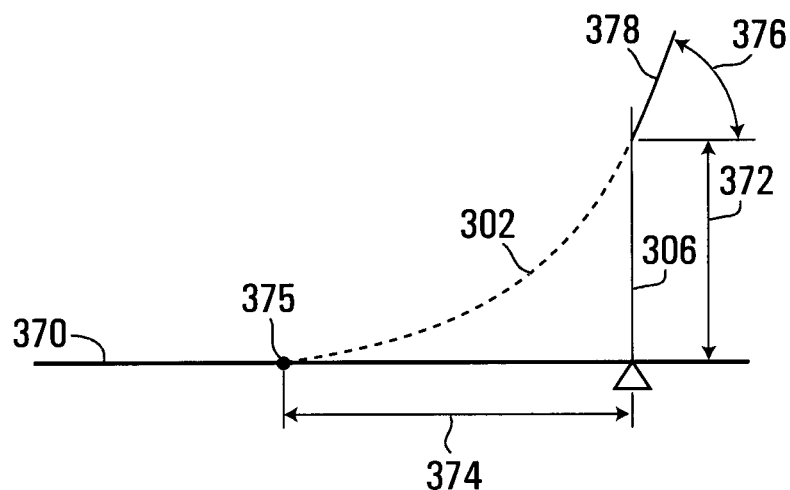
FIG. 9 is a graphical depiction of a first profile portion representing an edge shape in accordance with one embodiment of the invention.

The effect of the parametric controls 314 on the shape of the first profile portion 302 is described in more detail with reference to FIG. 9. The first profile portion 302 is referenced to a straight baseline 370, which generally corresponds to surface tangent, normal to the line 290 at the point corresponding to the graphical representation 300.

The height parameter defines a height 372 of the profile at the intended edge of the appliance indicated by the separator 306. The setback parameter defines a distance 374 from the separator 306 to a setback point 375 on the first profile portion that lies on the baseline 370. The angle parameter defines an angle 376 between an extension 378 of the first profile portion 302 and a line 380 parallel to the baseline 370.

The tension parameters T1 and T2 generally relate to the straightness of the first profile portion 302. Tension T1 affects the shape of the first profile portion 302 proximate the setback point 375 and tension T2 affects the shape of the first profile portion proximate the separator 306. Lower tension values of T1 and/or T2 locate the curvature of the first profile portion 302 proximate the setback point 375 and the separator 306 respectively. Higher tension values tend to move the curvature along the first profile portion 302 away from the setback point 375 and the separator 306 respectively. For example, if T1=T2=0, then the first profile portion 302 comprises a straight line between the setback point 375 and the separator 306. In one embodiment, the first and second profile portions 302 and 304 may be described by third order Bezier curves, for example.

Figure 10:
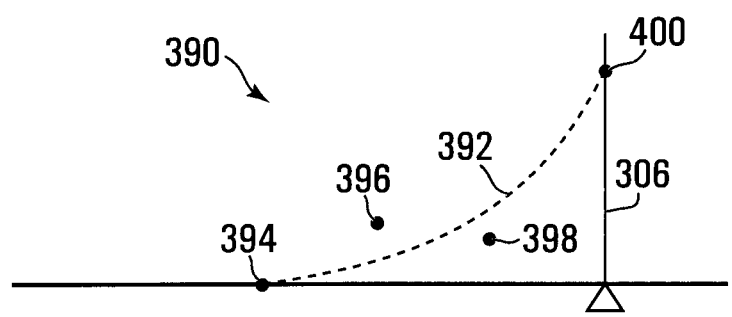
FIG. 10 is a graphical depiction of a first profile portion representing an edge shape in accordance with an alternative embodiment of the invention.

In an alternative embodiment the shape of the first profile portion may be affected by dragging control points displayed on the graphical representation 300. Referring to FIG. 10, a graphical representation of 390 includes a first profile portion 392 defined by a Bezier curve having control points 394, 396, 398, and 400. Control points 394 and 400 correspond to end points of the first profile portion 392, while control points 396 and 398 control the shape of the first profile portion. Other embodiments my implement a higher order Bezier curve having additional control points for a greater degree of control over the shape of the curve, or may use other curve types such as splines having control points located either on or off the curve or a combination thereof.

In embodiments where it is desired to vary edge shape of the edge along the line, graphical representations may be successively displayed for each of a plurality of points along the line. The parametric controls 314 for each successive graphical representation may be used to affect the edge shape in the region of a point corresponding to the currently displayed graphical representation. The edge shape may then be smoothly varied between successive points, as described later herein.

In other embodiments where the shape of the edge along the line is not varied, the edge shape corresponding to the line is generally represented by a single graphical representation 300.

Identifying Regions

Figure 11:
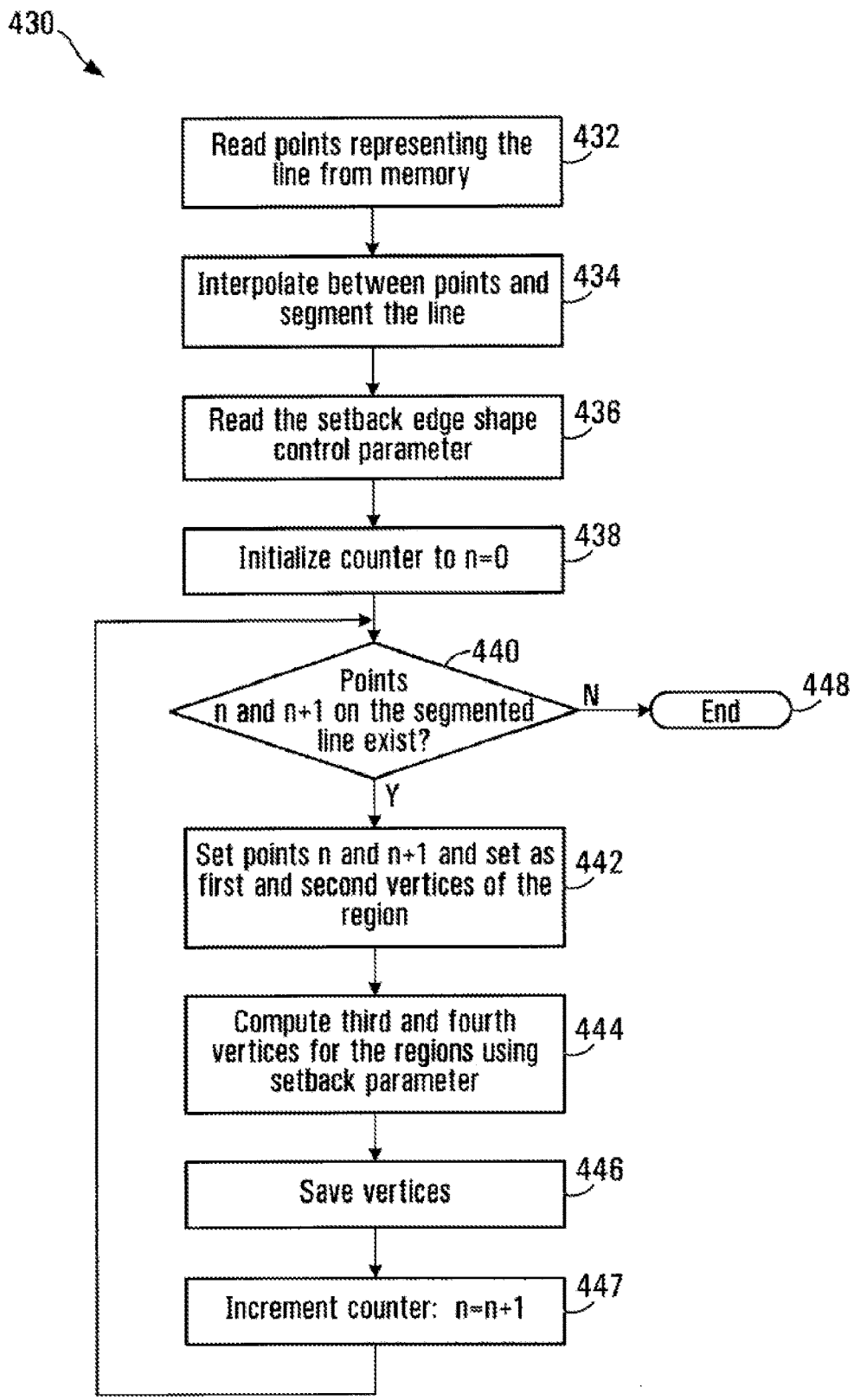
FIG. 11 is a flowchart representing blocks of codes for directing the processor circuit shown in FIG. 2 to execute a process for identifying the regions on opposite sides of the lines shown in FIG. 7.

Referring back to FIG. 5, block 246 of the process 240 is shown in greater detail in FIG. 11. Referring to FIG. 11, a flowchart of blocks of codes for directing the microprocessor 142 (shown in FIG. 2) to execute a process for identifying the regions on opposite sides of lines 290 and 292 is shown generally at 430.

The process begins at block 432, which directs the microprocessor 142 to read the points representing the line from the store 186 in the RAM 148.

Figure 12:
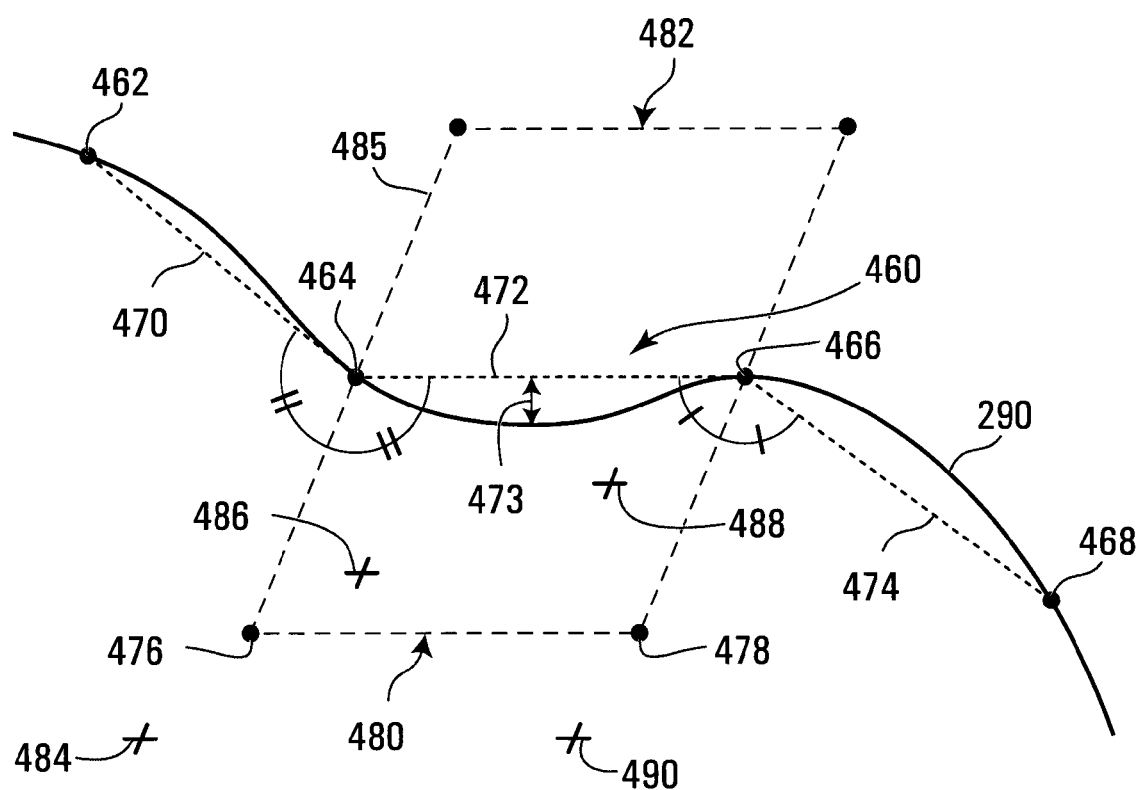
FIG. 12 is a schematic representation of a region.

Block 434 then directs the microprocessor 142 to segment the line. In this embodiment, the line 290 is initially defined by piecewise splines passing through a sparse set of points. Accordingly, when segmenting the line, block 434 directs the microprocessor 142 to first resample the line 290 to increase the density of points along the line by using the splines to interpolate between adjacent points read from the store 186. Referring to FIG. 12, an exemplary portion of a segmented line is shown generally at 460. The segmented line 460 includes points 462-468 all of which lie on the line 290. The points 462-468 define three line segments 470, 472 and 474, making up the segmented line 460. In the example shown, points 462 and 468 may have been points used to define the line 290, while points 464 and 466 may be interpolated points, for example.

In one embodiment the line 290 is recursively subdivided into equal length line segments until the segmented line meets a criterion for smoothness of the segmented line. For example, the smoothness criterion may be a reference threshold by which a mid-point of one of the segments 470-474 is permitted to deviate from the line 290 (i.e a distance indicated by arrow 473 in FIG. 12). The reference threshold may be set in accordance with a desired tolerance of the mold to be produced in the CAM machine 106, for example.

Block 434 then directs the microprocessor 142 to store the segmented line points in the store 188 of the RAM 148.

The process then continues at block 436, which directs the microprocessor 142 to read the setback edge shape control parameter from the store 190 in the RAM 148. Block 438 then directs the microprocessor 142 to initialize a counter for processing the points in the store 188 to n=0.

Block 440 then directs the microprocessor 142 to determine whether point n and point n+1 exist in the store 188, in which case the process continues at block 442. In the example shown in FIG. 12, point n corresponds to point 464, and point n+1 corresponds to point 466.

Block 442 directs the microprocessor 142 to set points n and n+1 as first and second vertices of the region.

Block 444 then directs the microprocessor 142 to compute coordinate locations of third and fourth vertices for the region. Referring to FIG. 12, a first region 480 and a second region 482 are shown in broken outline, the first and second regions extending along a surface of the mold on opposite sides of the line. In this embodiment region 480 is defined by the first, second, third and fourth vertices which are coincident with the surface of the mold representation, and this are not necessarily in the same plane.

The third vertex of the region 480 is shown at 476. A location of the third vertex 476 is computed by first bisecting an angle between the line segments 470 and 472 to determine a direction of a line 485 that passes through the third vertex, and then locating the third vertex at a distance along the line 485 corresponding to the setback control parameter read at block 436. A fourth vertex 478 is located in the same manner, as are third and fourth vertices for the region 482.

The process then continues at block 446, which directs the microprocessor 142 to save the vertices for the region in the store 192 of the RAM 148. Block 447 then directs the microprocessor 142 to increment the value of the counter n and then return to block 440 to process the next pair of points defining the segmented line 460 (i.e. points 466 and 468 in the example shown in FIG. 12).

If at block 440, the points n and n+1 on the segmented line do not exist, then all regions have been identified and the process 430 ends at 448.

Adjusting Coordinates

Figure 13:
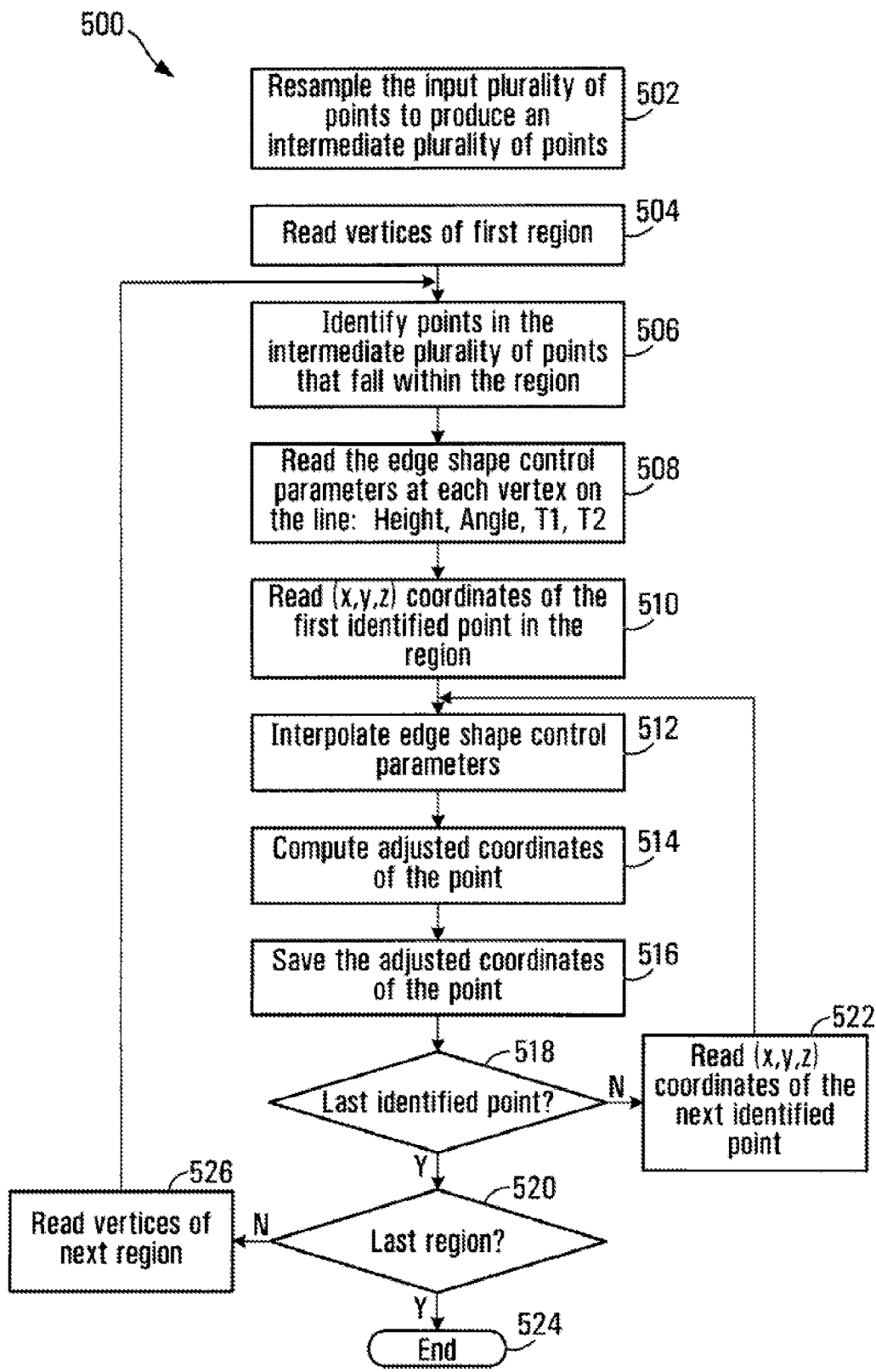
FIG. 13 is a flowchart representing blocks of codes for directing the processor circuit shown in FIG. 2 to execute a process for adjusting coordinates of points.

Referring back to FIG. 5, block 248 of the process 240 is shown in greater detail in FIG. 13. Referring to FIG. 13, a flowchart of blocks of codes for directing the microprocessor 142 (shown in FIG. 2) to execute a process for adjusting coordinates of points to produce a modified representation of the mold is shown generally at 500.

The process begins at block 502, which directs the microprocessor 142 to read the input plurality of points from the store 180 and to resample the input plurality of points to produce a more dense intermediate plurality of points for processing. In one embodiment resampling involves performing a cubic interpolation between adjacent points in the input plurality of points to produce additional points defining the surface of the mold. In other embodiments, where the input plurality of points is sufficiently dense to represent the mold surface to a desired resolution, the resampling may be omitted. Block 502 further directs the microprocessor 142 to save the intermediate plurality of points in the store 182 of the RAM 148.

Block 504 then directs the microprocessor 142 to read the vertices of the first region from the store 192 in the RAM 148.

The process then continues at block 506, which directs the microprocessor 142 to identify points in the intermediate plurality of points that fall within the first region. Referring back to FIG. 12, four points 484-490 in the intermediate plurality of points are shown. Two points, 486 and 488, fall within the region 480 and are thus identified for adjusting.

Referring back to FIG. 13, block 508 then directs the microprocessor 142 to read the height, angle, T1, and T2 edge shape control parameters for each vertex (i.e. the vertices at points 464 and 466) from the store 190 in the RAM 148. In embodiments where the edge shape control parameters vary along the line 290, each point 464 and 466 has an associated set of edge shape control parameters, which may differ slightly from one point to the next. In embodiments where the edge shape control parameters are uniformly applied along the line 290, a single set of edge shape control parameters may be used to define the shape of the edge at all points.

Referring back to FIG. 13, the process then continues at block 510, which directs the microprocessor 142 to read the (x,y,z) coordinates for the first identified point in the region 480 (for example the point 486).

Figure 14:
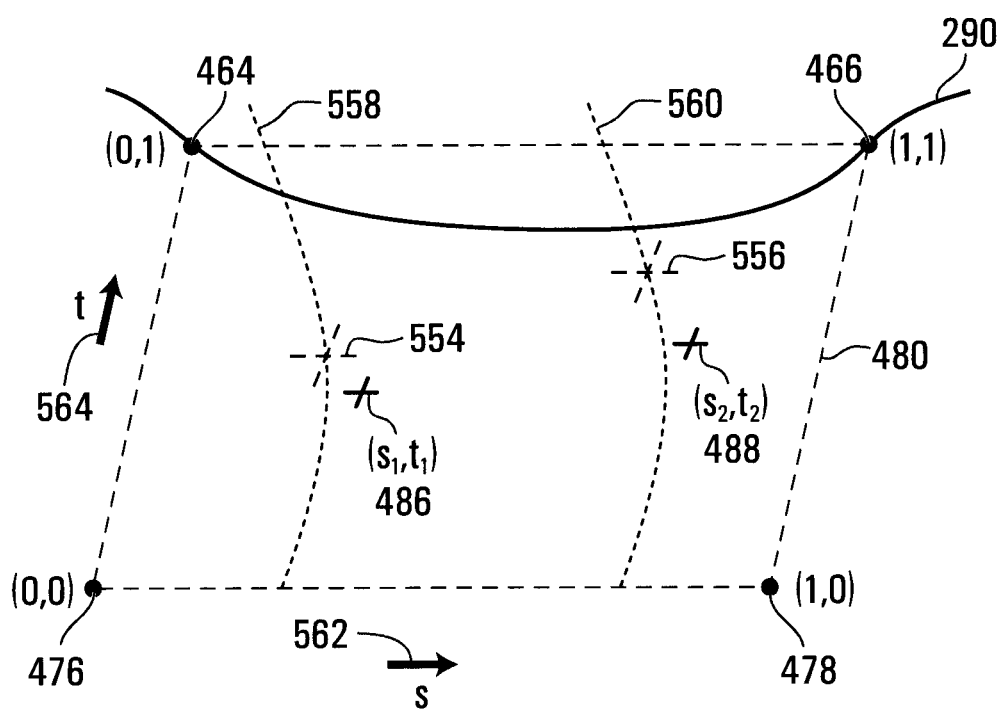
FIG. 14 is a schematic representation of a modified region and the region shown in FIG. 12.

Block 512 then directs the microprocessor 142 to interpolate the edge shape control parameters for the first identified point. The region 480 is shown in greater detail in FIG. 14. Referring to FIG. 14, the region 480 provides a local coordinate system for interpolating between the edge shape control parameters associated with each respective point 464 and 466. The coordinate system has an s axis extending in a direction 562 and at axis extending in a direction 564. In this embodiment, the point 476 is taken as the origin (0,0), and points 464, 466, and 478 are associated with s and t coordinates of (0,1), (1,1), and (1,0) respectively. Accordingly s and t coordinates ($s_1,t_1$) may be determined for the point 486, where $s_1$ and $t_1$ have values of between 0 and 1.

Interpolation of the edge shape control parameters involves using the $s_1$ coordinate of the point 486 to interpolate each of the edge shape control parameters (height, angle, T1, and T2) to produce a new set of edge shape control parameters at $s=s_1$ for the point 486.

The new set of edge shape control parameters define an interpolated profile portion 558 at $s=s_1$ which is associated with the point 486. The adjusted point 486 (shown as point 554 in FIG. 14) lies on the interpolated profile portion 558. The shape of the interpolated profile portion 558 is defined by a function such as a Bezier curve of third order, as described above in the first profile portion 302 in the graphical representation 300 shown in FIG. 9.

Block 514 then directs the microprocessor 142 to compute the coordinates for the modified point 554 by using the $t=t_1$ coordinate of the point 486 and function defining the interpolated profile portion 558 to compute an offset from the point 486 for computing the coordinates of the modified point 554. In embodiments where the interpolated profile portion 558 is defined by a Bezier curve, it is not possibly to explicitly determine the offset (such as finding roots of a polynomial, for example), and in such embodiment the offset to the coordinates may be determined by recursive subdivision of the profile portion.

Block 516 then directs the microprocessor 142 to save the adjusted coordinates of the point 486 (i.e. the coordinates of the point 554) to the store 184 of the RAM 148.

The process then continues at block 518, which directs the microprocessor 142 to determine whether the adjusted point is the last identified point in the region. If not, then block 514 directs the microprocessor 142 to block 522, which directs the microprocessor 142 to read the coordinates of the next identified point in the region 480 (i.e. the point 488). Block 522 then directs the microprocessor 142 to return to block 512, and blocks 512-518 are repeated for the next point to compute adjusted coordinates for the point 488, which is shown as a modified point 556 on an interpolated profile portion 560.

If at block 518, the adjusted point was the last identified point, then block 514 directs the microprocessor 142 to block 520. Block 520 directs the microprocessor 142 to determine whether the last region has been processed, in which case the process 500 ends at 524. If at block 520, there are still further regions to be processed, then the microprocessor 142 is directed to block 526. Block 526 directs the microprocessor 142 to read the vertices of the next region and then directs the microprocessor 142 to repeat blocks 506-522 for the next region.

Once all regions on both sides of the line 290 have been processed, the output plurality of points in the store 184 of the RAM 148 represent the modified surface of the mold.

Figure 15:
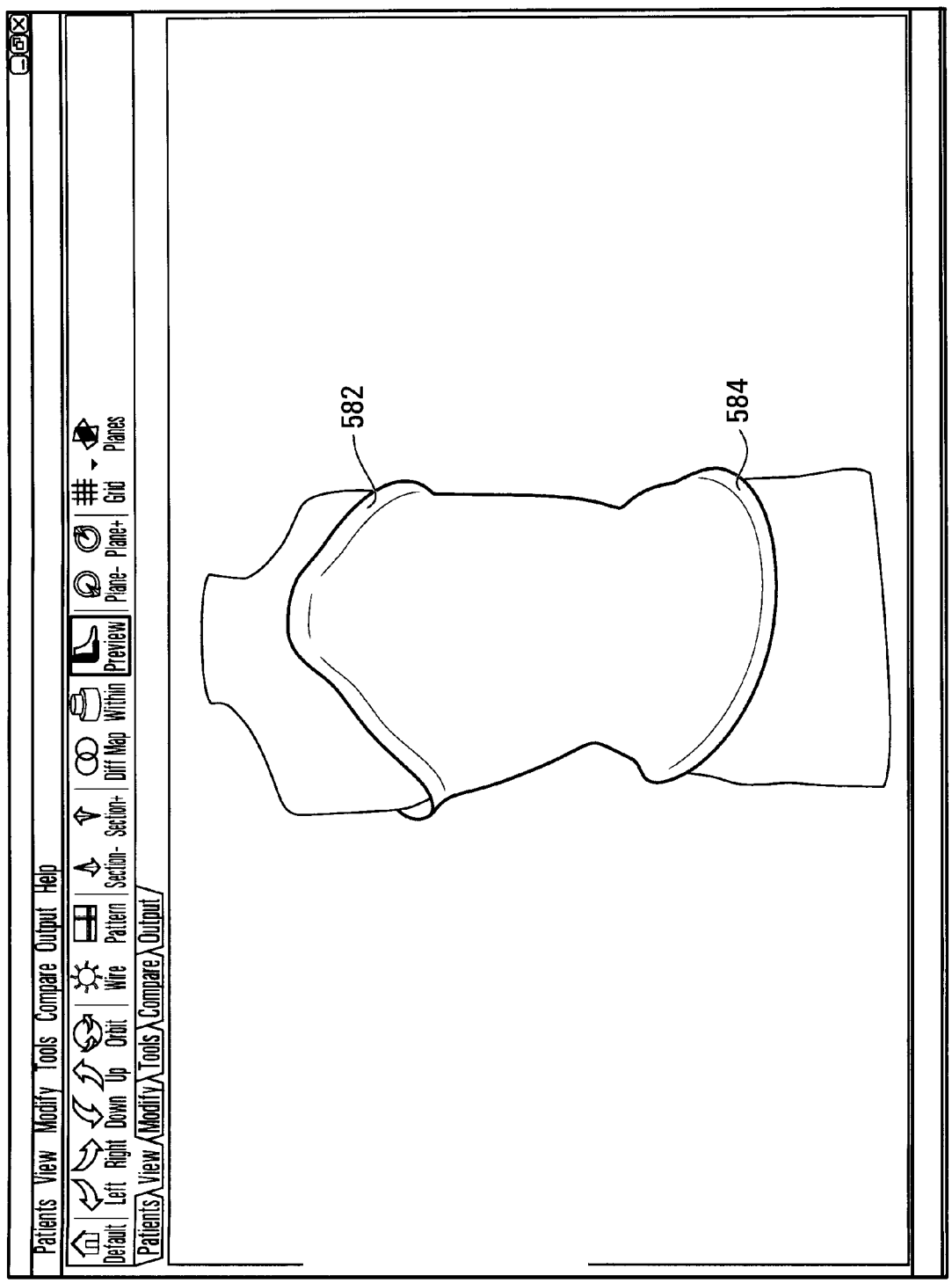
FIG. 15 is an exemplary view of a modified mold surface for the torso body part shown in FIG. 7.

Referring to FIG. 15, an exemplary view of a modified mold surface corresponding to the torso 108 shown in FIG. 7 is shown generally at 580. The modified mold representation includes modified edges 582 and 584 for forming flares in the appliance to be molded.

The output plurality of points in the store 184 may further be transformed into a set of carving instructions for controlling the CAM machine 106 shown in FIG. 1 for producing the mold.

The appliance is generally produced by covering the mold surface with a thermoplastic or other material and causing the material to conform to the mold surface while the thermoplastic is maintained in a pliable state. Once sufficiently cured on the mold (for example by cooling the mold), the appliance may be removed and, if necessary, trimmed or otherwise processed to from the final appliance.

In another embodiment, the microprocessor 142 causes the interface 166 of the processor circuit 140 (shown in FIG. 2) to further produce a signal at the output 168 encoded with a set of points defining the lines 290 and 292 that correspond to intended edges of the appliance. The mold with the cured appliance is then remounted in the CAM machine 106 and the cured appliance on the mold is automatically trimmed by the machine tool portion 118 in response to receiving the signal at the controller 122. Advantageously, in this embodiment having formed the mold, the intended edge locations are also defined and may be used to further automate the production of the appliance.

Advantageously, the above described processes facilitate the modification of a surface of a mold along an intended edge of an appliance to be produced using the mold. Furthermore, by providing a graphical representation of an edge shape at the intended edge of the appliance, a user is provided with a simple preview facilitating interactive changes to the shape of the edge.

While specific embodiments of the invention have been described and illustrated, such embodiments should be considered illustrative of the invention only and not as limiting the invention as construed in accordance with the accompanying claims.

What is claimed is:

1. A method for producing a representation of a mold for forming an appliance for a living body, the method comprising:
   causing a processor circuit to display a representation of a surface of the mold, said surface being defined by an input plurality of points stored in said processor circuit and representing a shape of the mold;
   receiving user input identifying a plurality of points representing a line corresponding to an intended edge of the appliance on said representation of said surface;
   receiving user input of a desired outward flare of the shape of said surface along said line, the outward flare having a variation along said line and being operable to provide relief between the edge of the appliance and the living body;
   causing said processor circuit to:
     identify regions extending away from said line along said surface on opposite sides of said line;
     determine points in said input plurality of points that fall within said regions;
     adjust at least one coordinate of points that fall within said regions to outwardly flare the shape of said surface along said line in accordance with said user input to produce a modified surface representation; and
   store said modified surface representation in a computer memory to produce a modified representation of the mold.

2. The method of claim 1 wherein receiving user input of a desired outward flare comprises displaying a graphical representation of said modified surface representation in said at least one region, said graphical representation representing a profile of said modified surface representation taken in a plane generally normal to said surface and extending along said surface on opposite sides of said line corresponding to said intended edge.

3. The method of claim 2 wherein displaying said graphical representation comprises displaying first and second profile portions, said first profile portion representing a profile of said modified surface representation up to a point coterminous with said intended edge of the appliance, and said second profile portion representing a profile of said modified surface representation adjacent said intended edge of the appliance.

4. The method of claim 3 further comprising affecting a shape of said first profile portion in response to first user input.

5. The method of claim 4 further comprising affecting a shape of said second profile portion in response to changes in said shape of said first profile portion.

6. The method of claim 4 wherein affecting said shape of said first profile portion comprises affecting said shape of said first profile portion in response to receiving user input of at least one of:
a height of said intended edge of said appliance;
a setback distance from said intended edge of said appliance;
an angle of said first profile portion at said intended edge of said appliance;
a tension parameter that affects a straightness of said first profile portion proximate said intended edge; and
a tension parameter that affects the straightness of the first profile portion distal to said intended edge.

7. The method of claim 4 further comprising affecting a shape of said second profile portion in response to second user input.

8. The method of claim 1 further comprising receiving said input plurality of points representing said shape of the mold.

9. The method of claim 1 further comprising transforming said modified representation of the mold into a set of instructions operable to control a computer aided manufacturing machine to produce the mold.

10. The method of claim 1 further comprising:
forming the appliance on the mold; and
transforming said points representing said line corresponding to an intended edge of the appliance on a surface of the mold into a set of instructions operable to control a computer aided manufacturing machine for trimming the appliance along said intended edge while mounted on the mold.

11. The method of claim 1 wherein identifying said regions comprises identifying a plurality of polygonal regions along said line.

12. The method of claim 11 wherein identifying said polygonal regions comprises identifying at least one quadrilateral shaped region along said line.

13. The method of claim 11 further comprising identifying at least one point on said surface that falls within said polygonal region.

14. The method of claim 1 further comprising receiving at least one parameter defining a desired alteration to said shape of said surface and wherein said adjusting comprises using said at least one parameter to compute said at least one coordinate.

15. An apparatus for producing a representation of a mold for forming an appliance for a living body, the apparatus comprising:
means for causing a processor circuit to display a representation of a surface of the mold, said surface being defined by an input plurality of points stored in said processor circuit and representing a shape of the mold;
means for receiving user input identifying a plurality of points representing a line corresponding to an intended edge of the appliance on the representation of said surface;
means for receiving user input of a desired outward flare of the shape of said surface along said line, the outward flare having a variation along said line and being operable to provide relief between the edge of the appliance and the living body;
means for causing said processor circuit to:
identify regions extending away from said line along said surface on opposite sides of said line;
determine points in said input plurality of points that fall within said regions;
adjust at least one coordinate of points that fall within said regions to outwardly flare the shape of said surface along said line in accordance with said user input to produce a modified surface representation in memory; and
store said modified surface representation to produce a modified representation of the mold.

16. The apparatus of claim 15 wherein said means for receiving user input comprises means for displaying a graphical representation of said modified surface representation in said at least one region, said graphical representation representing a profile of said modified surface representation taken in a plane generally normal to said surface and extending along said surface on opposite sides of said line corresponding to said intended edge.

17. The apparatus of claim 16 wherein said means for displaying said graphical representation comprises means for displaying first and second profile portions, said first profile portion representing a profile of said modified surface representation up to a point coterminous with said intended edge of the appliance, and said second profile portion representing a profile of said modified surface representation adjacent said intended edge of the appliance.

18. The apparatus of claim 15 further comprising means for transforming said modified representation of the mold into a set of instructions operable to control a computer aided manufacturing machine to produce the mold.

19. The apparatus of claim 15 further comprising:
means for forming the appliance on the mold; and
means for transforming said points representing said line corresponding to an intended edge of the appliance on a surface of the mold into a set of instructions operable to control a computer aided manufacturing machine for trimming the appliance along said intended edge while mounted on the mold.

20. The apparatus of claim 15 wherein said means for identifying said regions comprises means for identifying a plurality of polygonal regions along said line.

21. The apparatus of claim 20 further comprising means for identifying at least one point on said surface that falls within said polygonal region.

22. A non-transitory computer readable medium encoded with codes for directing a processor circuit to produce a representation of a mold for forming an appliance for a living body, the codes directing the processor circuit to:
display a representation of a surface of the mold, said surface being defined by an input plurality of points stored in said processor circuit and representing a shape of the mold;

receive user input identifying a plurality of points representing a line corresponding to an intended edge of the appliance on said representation of said surface;

receive user input of a desired outward flare of the shape of said surface along said line, the outward flare having a variation along said line and being operable to provide relief between the edge of the appliance and the living body;

identify regions extending away from said line along said surface on opposite sides of said line;

determine points in said input plurality of points that fall within said regions;

adjust at least one coordinate of points that fall within said regions to outwardly flare the shape of said surface along said line in accordance with said user input to produce a modified surface representation in memory; and store said modified surface representation in a computer memory to produce a modified representation of the mold.

23. An apparatus for producing a representation of a mold for forming an appliance for a living body, the apparatus comprising a processor circuit operably configured to:

display a representation of a surface of the mold, said surface being defined by an input plurality of points stored in said processor circuit and representing a shape of the mold;

receive user input identifying a plurality of points representing a line corresponding to an intended edge of the appliance on said representation of said surface;

receive user input of a desired outward flare of the shape of said surface along said line, the outward flare having a variation along said line and being operable to provide relief between the edge of the appliance and the living body;

identify regions extending away from said line along said surface on opposite sides of said line;

determine points in said input plurality of points that fall within said regions;

adjust at least one coordinate of points that fall within said regions to outwardly flare the shape of said surface along said line in accordance with said user input to produce a modified surface representation in memory; and store said modified surface representation in a computer memory to produce a modified representation of the mold.

24. The apparatus of claim 23 wherein said processor circuit is operably configured to receive user input by displaying a graphical representation of said modified surface representation in said at least one region, said graphical representation representing a profile of said modified surface representation taken in a plane generally normal to said surface and extending along said surface on opposite sides of said line corresponding to said intended edge.

25. The apparatus of claim 24 wherein said processor circuit is operably configured to display first and second profile portions, said first profile portion representing a profile of said modified surface representation up to a point coterminous with said intended edge of the appliance, and said second profile portion representing a profile of said modified surface representation adjacent said intended edge of the appliance.

26. The apparatus of claim 25 wherein said processor circuit is operably configured to affect a shape of said first profile portion in response to first user input.

27. The apparatus of claim 26 wherein said processor circuit is operably configured to affect a shape of said second profile portion in response to changes in said shape of said first profile portion.

28. The apparatus of claim 26 wherein said processor circuit is operably configured to affect said shape of said first profile portion in response to receiving user input of at least one of:
a height of said intended edge of said appliance in said at least one region;
a setback distance from said intended edge of said appliance;
an angle of said first profile portion at said intended edge of said appliance;
a tension parameter that affects a straightness of said first profile portion proximate said intended edge; and
a tension parameter that affects the straightness of the first profile portion distal to said intended edge.

29. The apparatus of claim 26 wherein said processor circuit is operably configured to affect a shape of said second profile portion in response to second user input.

30. The apparatus of claim 23 wherein said processor circuit is operably configured to receive said input plurality of points representing said shape of the mold.

31. The apparatus of claim 23 wherein said processor circuit is operably configured to transform said modified representation of the mold into a set of instructions operable to control a computer aided manufacturing machine to produce the mold.

32. The apparatus of claim 23 wherein said processor circuit is operably configured to transform said points representing said line corresponding to an intended edge of the appliance on a surface of the mold into a set of instructions operable to control a computer aided manufacturing machine for trimming a formed appliance along said intended edge while mounted on the mold.

33. The apparatus of claim 23 wherein said processor circuit is operably configured to identify a plurality of polygonal regions along said line.

34. The apparatus of claim 33 wherein said processor circuit is operably configured to identify at least one quadrilateral shaped region along said line.

35. The apparatus of claim 23 wherein said processor circuit is operably configured to receive at least one parameter defining a desired alteration to said shape of said surface and wherein said processor circuit is operably configured to adjust said at least one coordinate by using said at least one parameter to compute said at least one coordinate.

36. The apparatus of claim 33 wherein said processor circuit is operably configured to identify at least one point on said surface that falls within said polygonal region.

* * * * *